(12) United States Patent  (10) Patent No.: US 9,152,764 B2
Grant et al.  (45) Date of Patent: Oct. 6, 2015

(54) SYSTEMS AND METHODS FOR MANAGING DATA

(71) Applicants: Gregory Grant, Paradise Valley, AZ (US); John Vanderhoof, Scottsdale, AZ (US); Matthew John Seidel, Scottsdale, AZ (US)

(72) Inventors: Gregory Grant, Paradise Valley, AZ (US); John Vanderhoof, Scottsdale, AZ (US); Matthew John Seidel, Scottsdale, AZ (US)

(73) Assignee: PHOTON MEDICAL COMMUNICATIONS, INC., Scottsdale, AZ (US)

( * ) Notice: Subject to any disclaimer, the term of this patent is extended or adjusted under 35 U.S.C. 154(b) by 255 days.

(21) Appl. No.: 13/757,382

(22) Filed: Feb. 1, 2013

(65) Prior Publication Data

US 2013/0204951 A1  Aug. 8, 2013

Related U.S. Application Data

(60) Provisional application No. 61/594,171, filed on Feb. 2, 2012.

(51) Int. Cl.
  *G06F 19/00* (2011.01)
  *H04L 12/58* (2006.01)

(52) U.S. Cl.
  CPC .......... *G06F 19/327* (2013.01); *G06F 19/3406* (2013.01); *H04L 51/08* (2013.01)

(58) Field of Classification Search
  None
  See application file for complete search history.

(56) References Cited

U.S. PATENT DOCUMENTS

| | | | |
|---|---|---|---|
| 7,716,072 B1 | 5/2010 | Green, Jr. et al. | |
| 7,895,061 B2 | 2/2011 | Schoenberg | |
| 7,912,737 B2 | 3/2011 | Schoenberg | |
| 7,933,783 B2 | 4/2011 | Schoenberg | |
| 7,974,924 B2 | 7/2011 | Holla et al. | |
| 8,515,776 B2 | 8/2013 | Schoenberg | |
| 8,639,532 B2 | 1/2014 | Schoenberg | |
| 2001/0029322 A1 | 10/2001 | Iliff | |
| 2002/0065854 A1 | 5/2002 | Pressly | |
| 2002/0198473 A1 | 12/2002 | Kumar et al. | |
| 2005/0075544 A1* | 4/2005 | Shapiro et al. | 600/300 |
| 2007/0083403 A1 | 4/2007 | Baldwin et al. | |
| 2008/0021741 A1* | 1/2008 | Holla et al. | 705/3 |
| 2010/0305973 A1 | 12/2010 | McLaren et al. | |
| 2011/0251960 A1 | 10/2011 | Holla et al. | |
| 2011/0301982 A1 | 12/2011 | Green, Jr. et al. | |
| 2013/0297347 A1 | 11/2013 | Cardoza et al. | |

FOREIGN PATENT DOCUMENTS

| | | |
|---|---|---|
| CA | 2260838 | 1/1998 |
| WO | WO 98/02837 A1 | 1/1998 |
| WO | WO 01/37110 A1 | 5/2001 |
| WO | WO 03/017166 A1 | 2/2003 |
| WO | WO 2008/103811 A2 | 8/2008 |

* cited by examiner

*Primary Examiner* — Ebrahim Golabbakhsh
(74) *Attorney, Agent, or Firm* — Baker Hostetler LLP

(57) ABSTRACT

System and methods are disclosed, one method can comprise the steps of receiving a request for a diagnostic message, receiving a selection of diagnostic information, retrieving at least a portion of the selected diagnostic information, generating the requested diagnostic message, wherein the diagnostic message comprises the portion of the selected diagnostic information, and transmitting the requested diagnostic message.

28 Claims, 17 Drawing Sheets

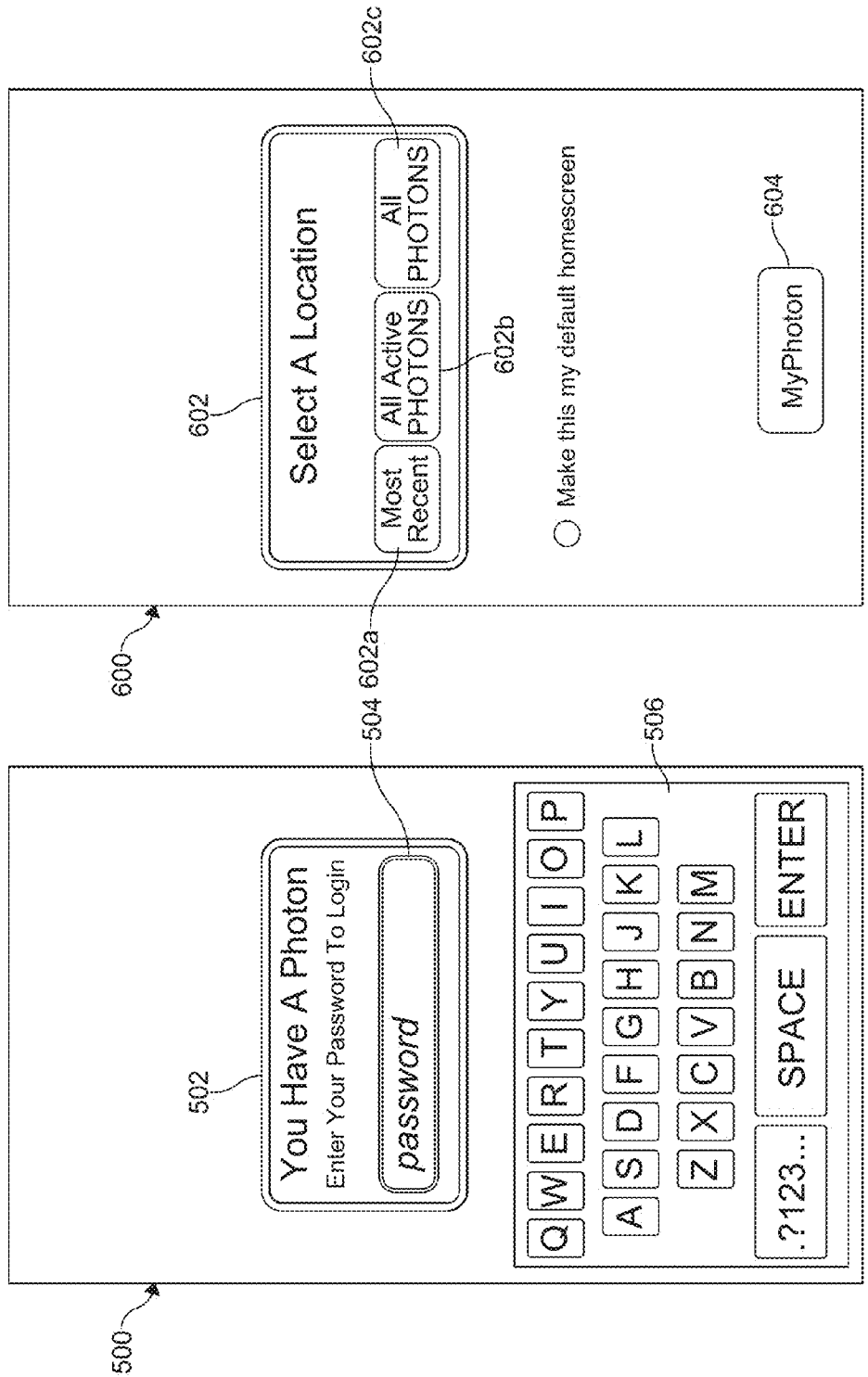

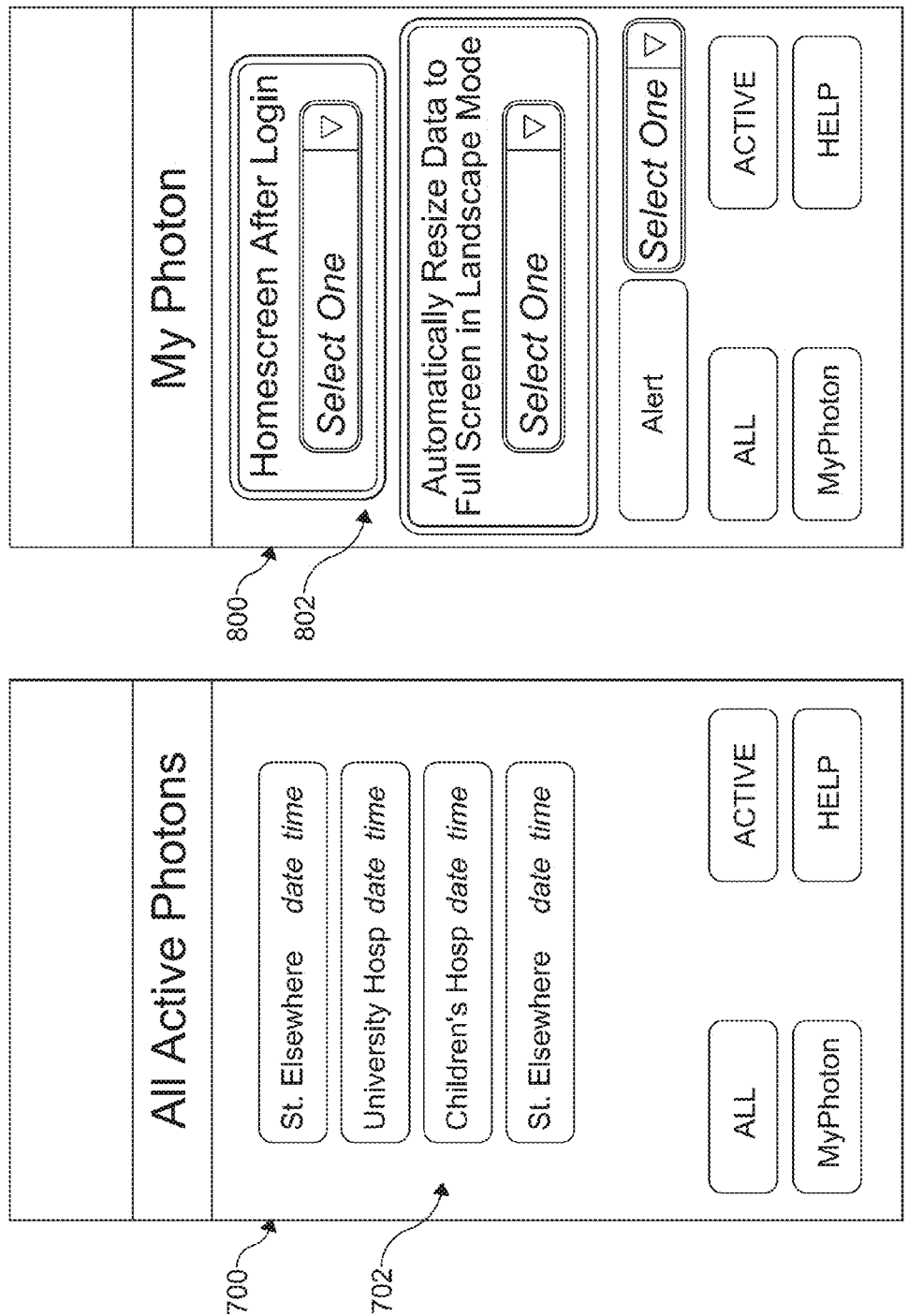

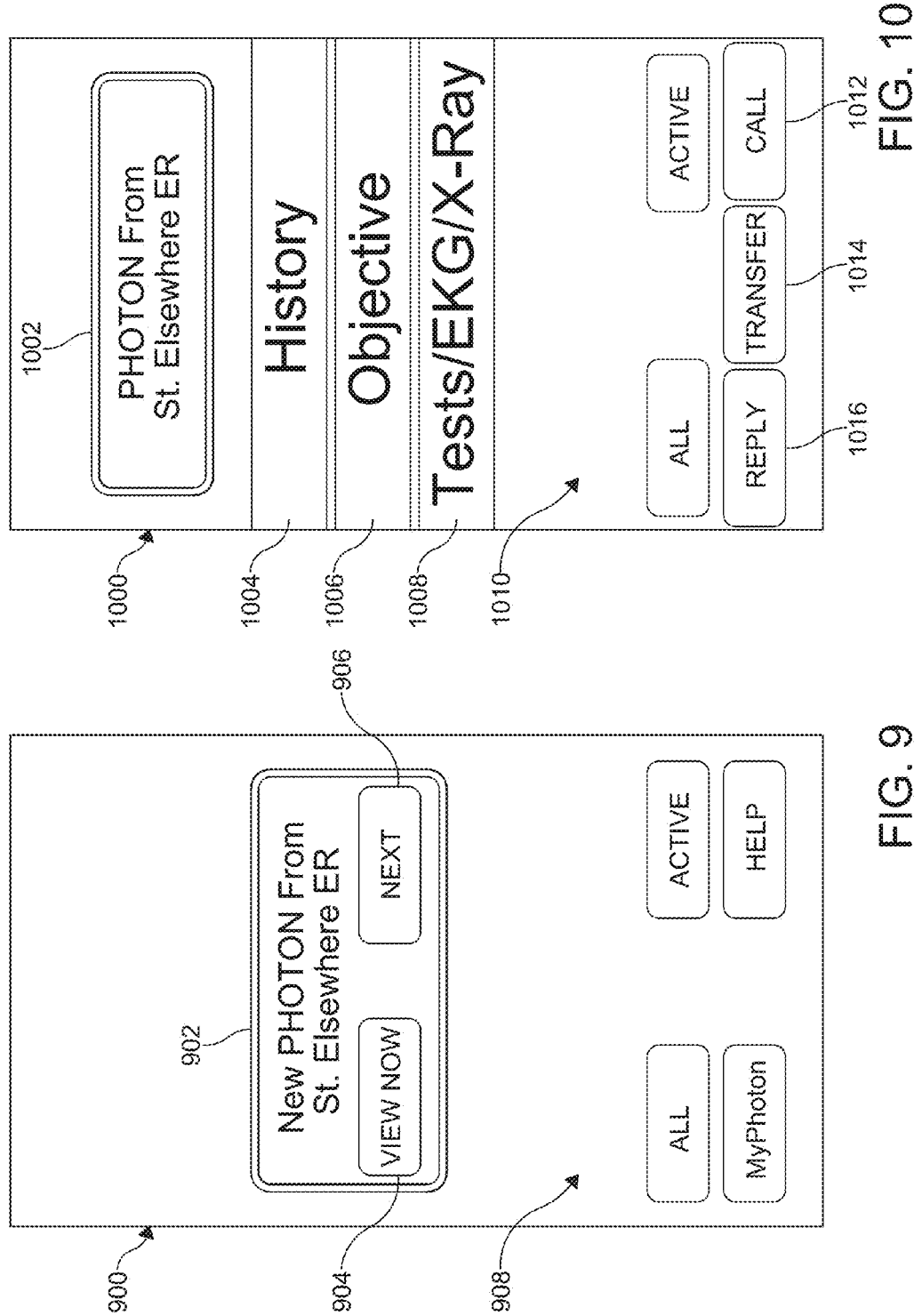

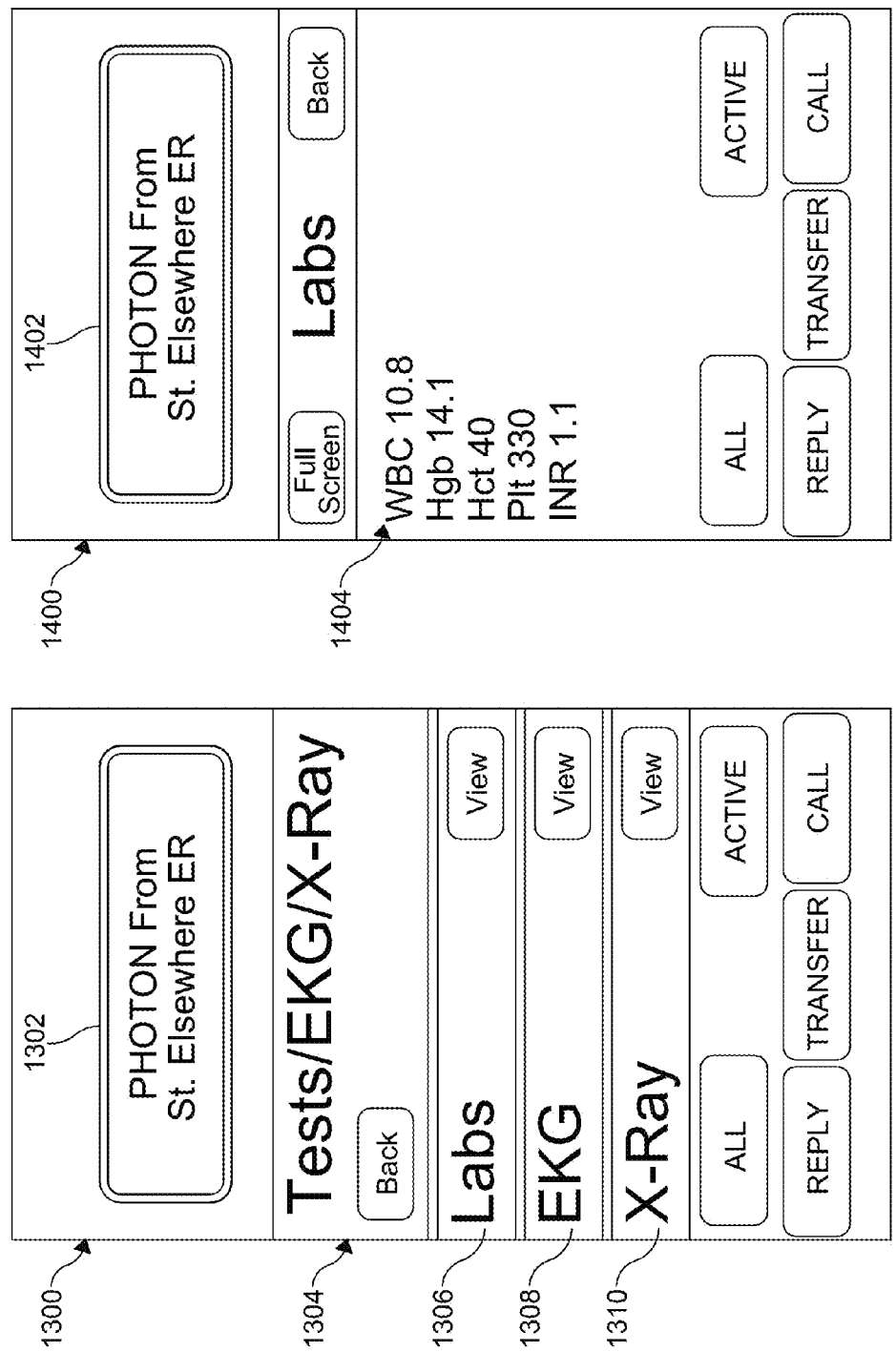

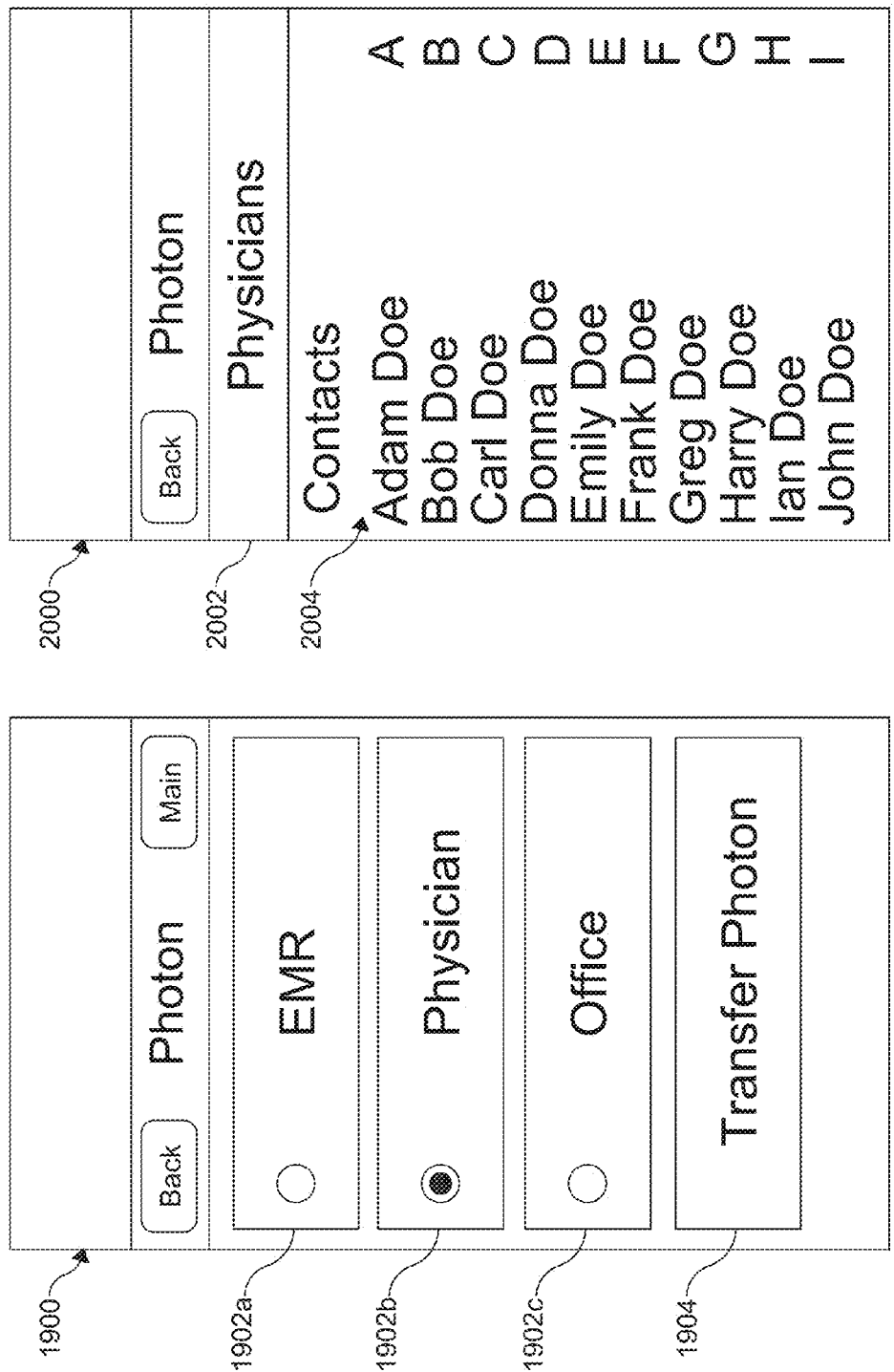

FIG. 26

Enter Information

Discription of Issue

Burns on Hands

Allergies
- ☐ Penicillin
- ☐ Peanuts
- ☐ Lactose
- ☐ Medicine

Requires Urgent Care? — 2602

FIG. 25

Create New P...

Step 1 - Enter Photon Data

Patient Information

Patient Code

Patient Code (required) — 2502

Patient Name

Patient Name (required) — 2502

Enter Information

Discription of Issue

| Requires Urgent Care? |
| --- |
| ☑ YES/NO |

| Upload Photo(s) (optional) | |
| --- | --- |
| Choose File | Photo |
| 1. | |
| Choose File | Photo |
| 2. | |
| Choose File | Photo |
| 3. | |
| Choose File | Photo |
| 4. | |
| Choose File | Photo |
| 5. | |

FIG. 27

SYSTEMS AND METHODS FOR MANAGING DATA

CROSS REFERENCE TO RELATED PATENT APPLICATION

This application claims priority to U.S. Provisional Application No. 61/594,171 filed Feb. 2, 2012, herein incorporated by reference in its entirety.

BACKGROUND

Communication of diagnostic information and/or patient information can be tedious and time consuming. Currently, many physicians and care-providers rely on paging devices and voice calls/messages to communicate diagnostic information and consultation information to and from hospitals, offices, and other physicians, care providers and users of such information. For example, in an emergency room, a physician seeing a patient with an orthopedic problem has to page the orthopedic surgeon on call. The physician can often wait approximately 5-10 minutes or even longer for the orthopedic surgeon to respond. When the orthopedic surgeon finally responds, the orthopedic surgeon is typically provided only basic diagnostic information about the patient about which the emergency room physician is consulting. The orthopedic surgeon then has to find means to view certain patient diagnostic information, most notably images, such as x-rays. Computer terminals are not always conveniently available. Accordingly, the orthopedic surgeon must travel to a local hospital or office or another area to access a computer for viewing patient information and diagnostic information. Once the orthopedic surgeon has viewed the patient and diagnostic information, the orthopedic surgeon must communicate a response to the consulting physician in the emergency room. Typically, the orthopedic surgeon can rely on telephone communication to respond to the consulting physician with consulting information.

The current methods of consultation and remote diagnosis do not provide an efficient means of communicating diagnostic information and consultation responses to and from remote users. Furthermore, the current systems and methods do not provide a means to coordinate availability and schedules of recipients of consultation requests. These and other shortcomings are addressed by the present disclosure.

SUMMARY

It is to be understood that both the following general description and the following detailed description are exemplary and explanatory only and are not restrictive, as claimed. In an aspect, provided are methods and systems for managing data and transmitting information. The system and methods of the present disclosure can be used to communication diagnostic information and response to and from remote users, such as physicians and care providers.

In an aspect, the systems and methods of the present disclosure minimize the communication inefficiencies and reduce the amount of wasted time that the emergency room physician and the patient have to deal with during their encounter. As an example, using the disclosed system and methods, an emergency room provider can determine that an orthopedist is necessary for consultation. The emergency room physician can chart like normal, but the data that is inputted into an electronic medical record (EMR) can be transmitted to a non-proprietary server, in which this information can be shared with any provider whether or not they have access to the proprietary system. The information inputted can be transmitted to the non-proprietary system with a single click of a mouse.

In an aspect, a discrete packet of information (e.g., Patient History Objective findings and Test results Over Network or PHOTON/Photon/photon) can be created once the emergency room provider requires consultation. As an example, the Photon can be sent to a cloud based server, which can be compatible with all or substantially all software platforms. The server can then push the Photon or packet of information to the remote physician or user, and the remote user is able to review the discrete packet of information with a user device, such as a smart device, tablet, computing device, or the like.

In an aspect, the remote user can review the information after logging-in in a secure manner. As an example, after reviewing the basic information and reviewing image information such as x-rays, the remote user can respond by transmitting a message (e.g., in a similar manner that the message was delivered) back to the original emergency room physician with diagnosis and disposition information. In an aspect, the emergency room physician can review the response provided by the remote user in a timely and secure manner.

In an aspect, a method can comprise receiving a request for information such as a diagnostic message. A selection of diagnostic information can also be received. At least a portion of the selected diagnostic information can be retrieved. The diagnostic message can be generated, wherein the diagnostic message comprises the portion of the selected diagnostic information. The diagnostic message can be transmitted to a recipient such as the requestor of information.

In an aspect, a method can comprise receiving a request for information such as a diagnostic message. Availability information relating to one or more of a plurality of users can be provided. A selection of at least one of the plurality of users can be received. A selection of diagnostic information can be received. Information relating to the selection of the at least one of the plurality of users and the selection of diagnostic information can be provided. The diagnostic message can be generated, wherein the diagnostic message comprises at least a portion of the selected diagnostic information. The diagnostic message can be transmitted to the at least one of the plurality of users selected.

In an aspect, a method can comprise receiving a first diagnostic message and receiving a second diagnostic message relating to the first diagnostic message. A plurality of response options can be provided, wherein at least one of the response options is customized based upon the first diagnostic message or the second diagnostic message, or both. A selection of one of the plurality of response options can be received. A responsive message can be provided based upon the selection of the one of the plurality of response options.

In an aspect, a method can comprise receiving a diagnostic message including diagnostic information. The diagnostic information can be rendered. A plurality of response options can be provided, wherein at least one of the response options is customized based upon the diagnostic information. A selection of one of the plurality of response options can be received. A message based upon the selection of the one of the plurality of response options can be generated and/or transmitted.

In another aspect, a system can comprise a memory for storing diagnostic information and a processor in communication with the memory. The processor can be configured to: receive a request for a diagnostic message; receive a selection of a first portion of the diagnostic information; retrieve a sub-portion of the selected first portion of the diagnostic information; generate the requested diagnostic message, wherein the diagnostic message comprises the sub-portion of the selected first portion of the diagnostic information; and provide the requested diagnostic message.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

BRIEF DESCRIPTION OF THE DRAWINGS

The accompanying drawings, which are incorporated in and constitute a part of this specification, illustrate embodiments and together with the description, serve to explain the principles of the methods and systems:

FIG. 5 is a representation of a user interface;
FIG. 6 is a representation of a user interface;
FIG. 7 is a representation of a user interface;
FIG. 8 is a representation of a user interface;
FIG. 9 is a representation of a user interface;
FIG. 10 is a representation of a user interface;
FIG. 13 is a representation of a user interface;
FIG. 14 is a representation of a user interface;
FIG. 19 is a representation of a user interface;
FIG. 20 is a representation of a user interface;
FIG. 25 is a representation of a user interface;
FIG. 26 is a representation of a user interface;
and
FIG. 27 is a representation of a user interface.

DETAILED DESCRIPTION

Figure 1:
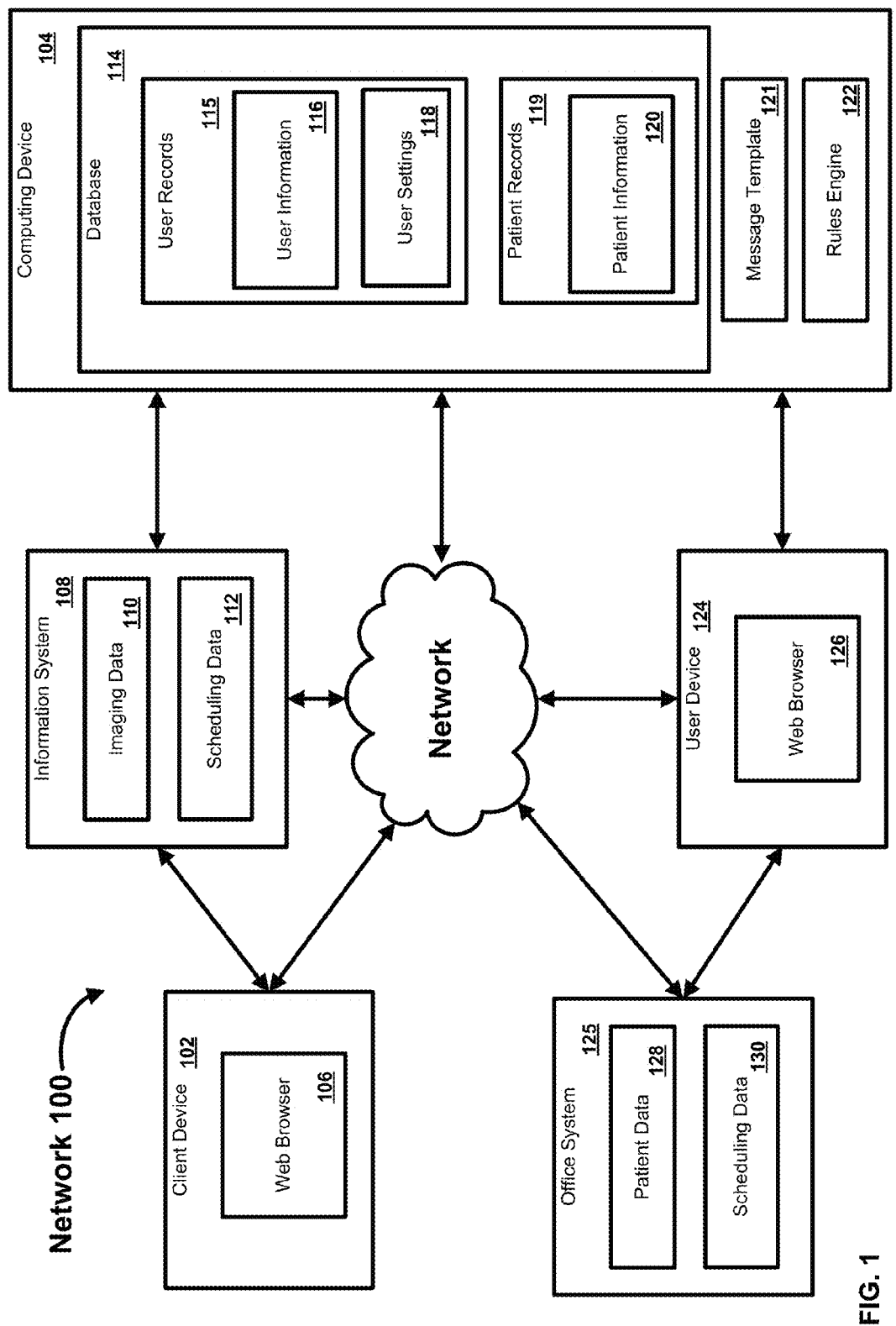
FIG. 1 is a block diagram of an exemplary network.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification, PHOTON/Photon is an acronym which can stand for Patient History Objective findings and Test results Over Network. As used herein, PHOTON/Photon can comprise patient information, diagnostic information, medical images, and the like. In general, the Photon system provides a way to communicate a packet of patient information in a secure manner between healthcare professionals and, more importantly, allows communication regarding that information. The PHOTON packet can comprise a subset data relating to a patient, such as a small, highly relevant, customized set of data regarding a specific problem that a patient may be experiencing. The term PHOTON/Photon is used for example and illustration only. PHOTON/Photon is not intended to limit the underlying data represented thereby. Any data can be represented and is not limited by the term PHOTON/Photon to any particular definition or classification.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the Examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

FIG. 1 illustrates various aspects of an exemplary network in which the present methods and systems can operate. The present disclosure relates to systems and methods for managing data such as medical related information. Those skilled in the art will appreciate that present methods may be used in systems that employ both digital and analog equipment. One skilled in the art will appreciate that provided herein is a functional description and that the respective functions can be performed by software, hardware, or a combination of software and hardware.

The system and network 100 can comprise a client device 102 in communication (e.g., directly and/or via a network) with a computing device 104 such as a server, for example. The computing device 104 can be disposed locally or remotely relative to the client device 102. As an example, the client device 102 and the computing device 104 can be in communication via a private or public network such as the Internet. Other forms of communications can be used such as wired and wireless telecommunication channels, for example.

In an aspect, the client device 102 can be an electronic device such as a computer, a server, a smartphone, a laptop, a tablet, or other device capable of communicating with the computing device 104. As an example, the client device 102 can comprise a web browser 106 for providing an interface to a user to interact with the client device 102 and/or the computing device 104. The web browser 106 can be any interface for presenting information to the user and receiving a user feedback, such as Internet Explorer, Mozilla Firefox, Google Chrome, Safari, or the like. Other software, hardware, and/or interfaces can be used to provide communication between the user and one or more of the client device 102 and the computing device 104. As an example, the web browser 106 can request or query various files from a local source and/or a remote source. As a further example, the client device 102 can be configured to transmit data to the computing device 104. Other devices and interfaces can be used to allow a user to intercommunicate with the computing device 104. In an aspect, the client device 102 can be authenticated via user/device credentials prior to communicating secure information to the computing device 104 or other device. As an example, the client device 102 can comprise software to facilitate secure communication and/or authentication.

In an aspect, the client device 102 can be configured to communicate (e.g., directly and/or via a network) with an information system 108 (e.g. emergency room information system, hospital information system, imaging system, scheduling system, etc.). As an example, the information system 108 can comprise a database. As a further example, the information system 108 can comprise hardware (e.g., terminal) and or software components for storing and/or processing patient information such as imagining data 110 (e.g., x-rays, CT scans, EKGs, etc.). Other information can be stored and/or processed by the information system 108, such as scheduling data 112 (e.g., relating to "on-call" physicians, employee schedules, or other schedule and time related data). In an aspect, the client device 102 can send/receive information to/from the information system 108 for storing information in the information system 108 and/or retrieving information from the information system 108. As an example, the client device 102 can comprise an instruction set or rule set to control the transmission of data to/from the information system 108. As a further example, the client device 102 can be configured to push data to the information system 108 when an input data is received by the client device 102. Any data or portion of data inputted to the client device 102 can be selectively and/or automatically transmitted to the information system 108 or another storage medium. In an aspect, the client device 102 can be authenticated via user/device credentials prior to communicating secure information to the information system 108 or other device. As an example, the client device 102 can comprise software to facilitate secure communication and/or authentication.

In an aspect, the information system 108 can comprise data relating to a hospital, clinic, medical facility, emergency room, or other professional environment. Other data can be stored and processed by the information system 108. As an example, the information system 108 can be located remotely from the client device 102. As a further example, the information system 108 can be integrated with the client device 102 or in communication with the client device over a local network.

In an aspect, the computing device 104 can be a server for communicating with the client device 102. As an example, the computing device 104 can be configured to receive message requests (e.g. diagnostic messages) from another device, such as the client device 102. The computing device 104 can be configured to process the message request and generate/transmit a message in response to the request. As a further example, the computing device 104 can manage the intercommunication between the client device 102 and a database 114 for sending and receiving data therebetween. In an aspect, the database 114 can store a plurality of files (e.g. web pages). As an example, the client device 102 can request a file from the database 114. As a further example, the client device 102 can retrieve a file from the database 114.

In an aspect, the database 114 can store a plurality of user records 115. As an example, one or more of the user records 115 can comprise user information 116 relating to a client or other user. In an aspect, the user information 116 can comprise contact information, professional/license information, preferences, and mailing lists, for example.

In an aspect, one or more user records 115 can comprise user settings 118 relating to one or more users, physicians, consultants, healthcare providers, professionals, message recipients, and the like. As an example, the user settings 118 can comprise demographic information, contact information, user credentials or login credentials, a unique identifier or password, and preferences (e.g. message preferences, including pre-defined information fields to be populated and included in diagnostic messages).

In an aspect, the database 114 can store a plurality of patient records 119. As an example, one or more of the patient records 119 can comprise patient information 120 relating to a client or other user. In an aspect, the patient information 120 can comprise contact information, medical information, insurance information, preferences, and other information relating to patient and/or treatment, for example. Other information can be stored in the database 114 and/or associated with a particular patient record 119.

In an aspect, one or more message templates 121 can be retrieved by the computing device 104 (e.g., stored in the database 114 or in other storage devices/media). As an example one or more message templates 121 can comprise a pre-defined layout of a plurality of information fields. As a further example, each of the message templates 121 can comprise a plurality of information fields. In an aspect, the information fields of the message templates can be populated from data stored in the database 114. However, the information fields of the message templates 121 can be populated from any data source. Any number of information fields representing any data or information can be included in the message templates 121. Any number of message templates 121 can be stored and/or generated. As an example, one or more message templates 121 can comprises one or more data fields relating to one or more of the following: demographics, such as first name, middle name, last name, date of birth, SSN, address, driver's license information, insurance information, second insurance information, health information; chief complaint (e.g. what is patient is primarily complaining about?); history of present illness (e.g. what happened to the patient? how did it happen? where did it happen? associated symptoms, pain level, etc.); past medical history; past surgical history; medications; allergies: social history (e.g., history of smoking, drinking, drugs, employment, living situation); review of systems (e.g. history of fever, headache, chest pain, shortness of breath; physical examination information; general appearance (e.g., what the patient looks like—thin, obese, disheveled, clean, etc.); mood and affect; psychiatric information; neurologic exam; integumentary exam (skin); cardiovascular exam (blood vessels); studies, including labs such as complete blood count, blood electrolytes, liver function tests, urinalysis, drug screen, alcohol level, arterial blood gas, cardiac enzymes, troponin, erythrocyte sedimentation rate, C-reactive protein; imaging including X-rays, MRI, CT, ultrasound, echocardiogram, bone scan, PET scan, EKG; audio/video, clinical photographs; impression/diagnosis, such as triage nurse impression, physician assistant impression, ED physician impression; ED Action Plan; and/or disposition and follow-up appointment.

In an aspect, the message can comprise complete patient encounter information. The users that will receive the diagnostic message can have the option of selecting a discrete amount of highly relevant information for their particular specialty. Other users can choose to accept all the information. Each specialty will be different from each other with regards to what information is most relevant.

In an aspect, the computing device 104 can comprise a rules engine 122 for applying one or more rules/filter/instructions/settings to the messages (e.g., diagnostic messages). As an example, the rules engine 122 can retrieve preferences and instructions from the user settings 118 in order to customize a particular message format and/or content associated with a particular recipient. In this way, a recipient can define a particular information and formation of the information to be included in any messages received by the particular recipient. As a further example, certain information is customizable and other information and formatting is standard. In an aspect the rules engine 122 can customize format/content based upon any number of rules or instructions, such as information about the sender or recipient, information specific to the client or patient/subject of the message, specialty, time of day, means of communication, level of urgency, and other rules.

In an aspect, a user device 124 can be in communication with the computing device 104. The computing device 104 can be disposed locally or remotely relative to the user device 124. As an example, the user device 124 and the computing device 104 can be in communication via a private or public network, such as the Internet. Other forms of communications can be used such as wired and wireless telecommunication channels, for example.

In an aspect, the user device 124 can be an electronic device, such as a computer, a server, a smartphone, a laptop, a tablet, or other device capable of communicating with the computing device 104. As an example, the user device 124 can comprise a communication element, such as web browser 126 for providing an interface to a user to interact with the client device 102, the computing device 104, the information system 108, and/or an office system 125. The web browser 126 can be any interface for presenting information to the user and receiving a user feedback, such as Internet Explorer, Mozilla Firefox, Google Chrome, Safari, or the like. Other software, hardware, and/or interfaces can be used to provide communication between the user and one or more of the user device 124 and the client device 102, the computing device 104, the information system 108, and/or an office system 125. As an example, the web browser 126 can request or query various files from a local source and/or a remote source. As a further example, the user device 124 can be configured to transmit data to the computing device 104 via various protocols and over various networks. Other devices and interfaces can be used to allow a user to intercommunicate with the computing device 104. In an aspect, the client device 102 can be authenticated via user/device credentials prior to communicating secure information to the client device 102, the computing device 104, the information system 108, and/or an office system 125, or other device. As an example, the client device 102 can comprise software to facilitate secure communication and/or authentication. In an aspect, a user can use the user device 124 to communicate with client device 102 to transmit/receive data therebetween. As an example, the client device 102 can operate as a proxy for the user device 104 when communicating with the computing device 104, the information system 108, and/or an office system 125. As a further example, the user device 124 may not be authenticated with one or more of the computing device 104, the information system 108, and/or an office system 125. Accordingly, the user device 124 can communicate information to the client device 102 using a unique identifier (e.g., temporary or persistent), and the client device 102 can communication with one or more of the computing device 104, the information system 108, and/or an office system 125 on behalf of the user device 124.

In an aspect, the office system 125 can comprise information relating to a particular professional office, such as a medical office, law office, or other group of professionals. As an example, the office system 125 can be located remote from the information system 108 and/or the computing system 104. In an aspect, the office system 125 can comprise a patient data 128 (e.g., EMR) and/or a scheduling data 130. As an example, the patient data 128 can relate to a client or other user. In an aspect, patient data 128 can comprise contact information, medical information, insurance information, preferences, and other information relating to patient and/or treatment, for example. Other information can be stored in office system 125 and/or associated with a particular user/patient. As a further example, the scheduling data 130 can comprise information relating to a schedule of one or more physicians, healthcare providers, staff, technicians, professionals, or other office personnel. In an aspect, the client device 102 can be authenticated via user/device credentials prior to communicating secure information to the office system 125 or other device. As an example, the client device 102 can comprise software to facilitate secure communication and/or authentication.

Figure 2:
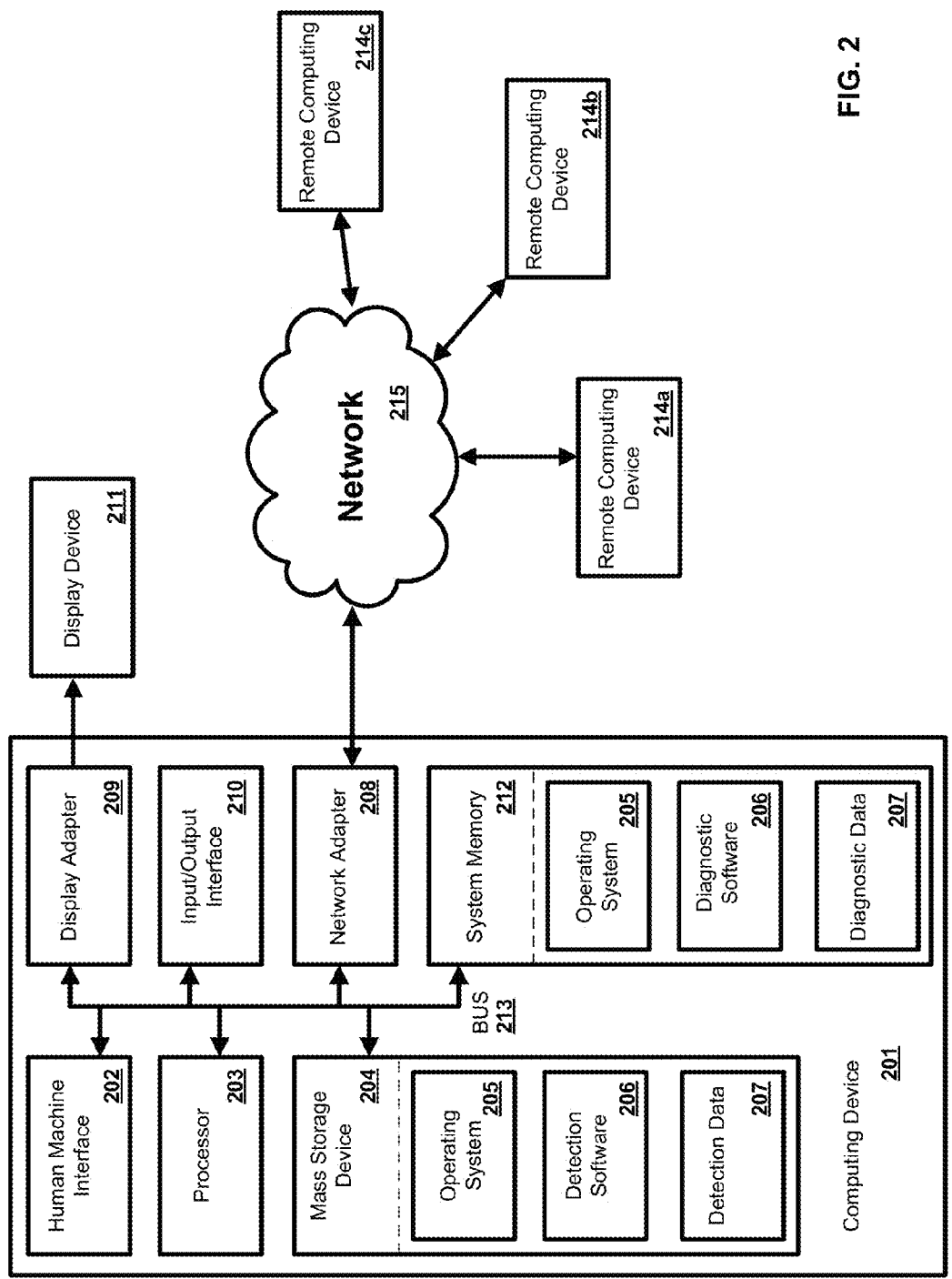
FIG. 2 is a block diagram of an exemplary computing device.

In an exemplary aspect, the methods and systems can be implemented on a computing system such as computing device 201 as illustrated in FIG. 2 and described below. By way of example, one or more of the client device 102, the computing device 104, and the user device 124 of FIG. 1 can be a computer as illustrated in FIG. 2. Similarly, the methods and systems disclosed can utilize one or more computers to perform one or more functions in one or more locations. FIG. 2 is a block diagram illustrating an exemplary operating environment for performing the disclosed methods. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods and systems can be operational with numerous other general purpose or special purpose computing system environments or configurations. Examples of well known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed systems and methods can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including memory storage devices.

FIG. 2 is a block diagram illustrating an exemplary operating environment for performing the disclosed methods. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods and systems can be operational with numerous other general purpose or special purpose computing system environments or configurations. Examples of well known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed systems and methods can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems and methods disclosed herein can be implemented via a general-purpose computing device in the form of a computer 201. The components of the computer 201 can comprise, but are not limited to, one or more processors or processing units 203, a system memory 212, and a system bus 213 that couples various system components including the processor 203 to the system memory 212. In the case of multiple processing units 203, the system can utilize parallel computing.

The system bus 213 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 213, and all buses specified in this description can also be implemented over a wired or wireless network connection and each of the subsystems, including the processor 203, a mass storage device 204, an operating system 205, financial software 206, financial data 207, a network adapter 208, system memory 212, an Input/Output Interface 210, a display adapter 209, a display device 211, and a human machine interface 202, can be contained within one or more remote computing devices 214a,b,c at physically separate locations, connected through buses of this form, in effect implementing a fully distributed system.

The computer 201 typically comprises a variety of computer readable media. Exemplary readable media can be any available media that is accessible by the computer 201 and comprises, for example and not meant to be limiting, both volatile and non-volatile media, removable and non-removable media. The system memory 212 comprises computer readable media in the form of volatile memory, such as random access memory (RAM), and/or non-volatile memory, such as read only memory (ROM). The system memory 212 typically contains data such as financial data 207 and/or program modules such as operating system 205 and financial software 206 that are immediately accessible to and/or are presently operated on by the processing unit 203.

In another aspect, the computer 201 can also comprise other removable/non-removable, volatile/non-volatile computer storage media. By way of example, FIG. 2 illustrates a mass storage device 204 which can provide non-volatile storage of computer code, computer readable instructions, data structures, program modules, and other data for the computer 201. For example and not meant to be limiting, a mass storage device 204 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 204, including by way of example, an operating system 205 and financial software 206. Each of the operating system 205 and financial software 206 (or some combination thereof) can comprise elements of the programming and the financial software 206. Financial data 207 can also be stored on the mass storage device 104. Financial data 207 can be stored in any of one or more databases known in the art. Examples of such databases comprise. DB2®, Microsoft® Access, Microsoft® SQL Server, Oracle®, mySQL, PostgreSQL, and the like. The databases can be centralized or distributed across multiple systems.

In another aspect, the user can enter commands and information into the computer 201 via an input device (not shown). Examples of such input devices comprise, but are not limited to, a keyboard, pointing device (e.g., a "mouse"), a microphone, a joystick, a scanner, tactile input devices such as gloves, and other body coverings, and the like. These and other input devices can be connected to the processing unit 203 via a human machine interface 202 that is coupled to the system bus 213, but can be connected by other interface and bus structures, such as a parallel port, game port, an IEEE 1394 Port (also known as a Firewire port), a serial port, or a universal serial bus (USB).

In yet another aspect, a display device 211 can also be connected to the system bus 213 via an interface, such as a display adapter 209. It is contemplated that the computer 201 can have more than one display adapter 209 and the computer 201 can have more than one display device 211. For example, a display device can be a monitor, an LCD (Liquid Crystal Display), or a projector. In addition to the display device 211, other output peripheral devices can comprise components such as speakers (not shown) and a printer (not shown) which can be connected to the computer 201 via Input/Output Interface 210. Any step and/or result of the methods can be output in any form to an output device. Such output can be any form of visual representation, including, but not limited to, textual, graphical, animation, audio, tactile, and the like.

The computer 201 can operate in a networked environment using logical connections to one or more remote computing devices 214a,b,c. By way of example, a remote computing device can be a personal computer, portable computer, a server, a router, a network computer, a peer device or other common network node, and so on. Logical connections between the computer 201 and a remote computing device 214a,b,c can be made via a local area network (LAN) and a general wide area network (WAN). Such network connections can be through a network adapter 208. A network adapter 208 can be implemented in both wired and wireless environments. Such networking environments are conventional and commonplace in offices, enterprise-wide computer networks, intranets, and the Internet 215.

For purposes of illustration, application programs and other executable program components such as the operating system 205 are illustrated herein as discrete blocks, although it is recognized that such programs and components reside at various times in different storage components of the computing device 201, and are executed by the data processor(s) of the computer. An implementation of financial software 206 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems can employ artificial intelligence (AI) techniques such as machine learning and iterative learning. Examples of such techniques include, but are not limited to expert systems, case based reasoning. Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

Figure 3A:
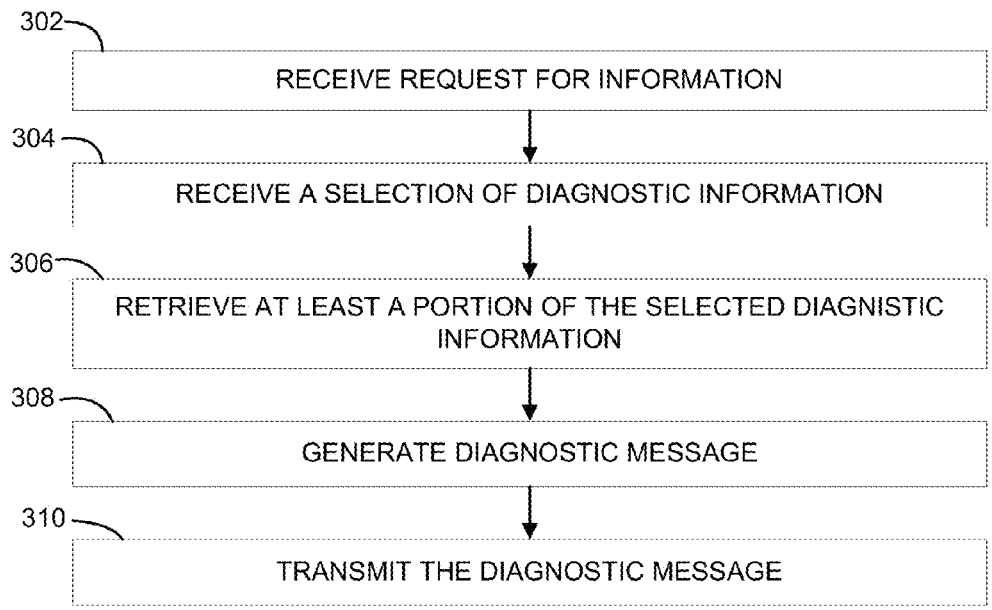
FIG. 3A is a flow chart of an exemplary method.

In an aspect, FIG. 3A illustrates an exemplary method for generating and/or transmitting a message such as a diagnostic message or consultation message. In an aspect, in step 302, a request for information such as a message (e.g., diagnostic message, PHOTON, or the like) can be received, for example, by the computing device 104. As an example, the request can be received by the client device 102 or the user device 124. However, other devices and systems can be used to transmit the request. In an aspect, an interface is provided to allow a user/client to request a message. As an example, the client device 102 can include a user interface with a "request message" icon or engageable button. Other means of requesting the message can be used. As a further example, once a user/client selects the "request message" icon, the user/client can be prompted to provide and/or select particular diagnostic information to be included in the message.

In an aspect, the client can select/provide a particular information (e.g., diagnostic information, requester information, recipient information, etc.) to be included in the message and can submit the request for the message. In an aspect, in step 304, the selection/provision of information can be received, for example, by the computing device 104. As a further example, the computing device 104 can process the request to retrieve at least a portion of the selected information (e.g., diagnostic information), at step 306. In an aspect, the diagnostic information can comprises one or more of patient data, medical data, and a medical image such as an EKG, an X-ray and/or other medical images, audio or video.

In an aspect, the computing device 104 can retrieve the selected/requested diagnostic information from any storage medium(s). As an example, at least a portion of the selected/requested diagnostic information can be retrieved from the database 114. In an aspect, the user settings 118 associated with an intended recipient of the diagnostic message can be applied to the selected/requested diagnostic information. For example, a particular user setting 118 may include pre-defined information fields that should be included in the messages that are sent to the user/recipient associated with the particular user setting 118. Accordingly, even though the selected/requested diagnostic information includes different information, the user setting 118 can take priority to retrieve a subset of the selected/requested diagnostic information to be included in the message.

In an aspect, in step 308, a diagnostic message can be generated. As an example, the diagnostic message can comprise the portion of the selected diagnostic information. However, any information can be included. In an aspect, the user settings 118 associated with an intended recipient of the diagnostic message are applied to the selected/requested diagnostic information. For example, a particular user setting 118 may include pre-defined information fields to be included in the messages that are sent to the user/recipient associated with the particular user setting 118. Accordingly, even though the selected/requested diagnostic information includes different information, the user setting 118 can take priority to retrieve a subset of the selected/requested diagnostic information to be included in the message.

In an aspect, computing device 104 and/or database 114 can comprise specialty templates for the messages. The specialty templates can be specifically created for each specialty in a particular profession, such as medicine/healthcare. For example, an orthopedic template can consist of basic patient information as well as x-rays. As a further example, a cardiology template can consist of basic patient information as well as an EKG or echocardiogram. As a further example, a gastroenterology template will consist of basic information as well as an abdominal x-ray or abdominal CT and perhaps lab information. The specialty templates can be created prior to implementation of the specific specialty message generation. Templates can be changed as needed. In an aspect, the requester of a message can select a pre-defined template for sending to an intended recipient.

In step 310, the message (e.g., diagnostic message) can be transmitted. As an example, the message can be transmitted to a recipient identified by the requester of the message. The message can be transmitted over any communication path or network such as the Internet and/or mobile telephone network.

In an aspect, the computing device 104 or other device can track a status of one or more transmitted messages. As an example, the following information can be tracked, time stamped, and or stored: date/time the message was generated/sent/received/forwarded/replied to; location (GPS) of requester/recipient; recipient device: receipt confirmation: read confirmation: no-read alert/feedback; and returned message alert. Other information and a feedback can be tracked/stored. In an aspect, the tracked information can be used to document the timeline of the electronic consultation and provide some medicolegal cushion for the emergency room providers who have to rely strictly on a verbal order or recommendation from the consultants. As an example, consultants who render medical decisions verbally can now be formally documented in the medical record when they made their diagnosis and what kind of treatment was recommended. This provides an enormous amount of medicolegal relief to ED providers.

Figure 3B:
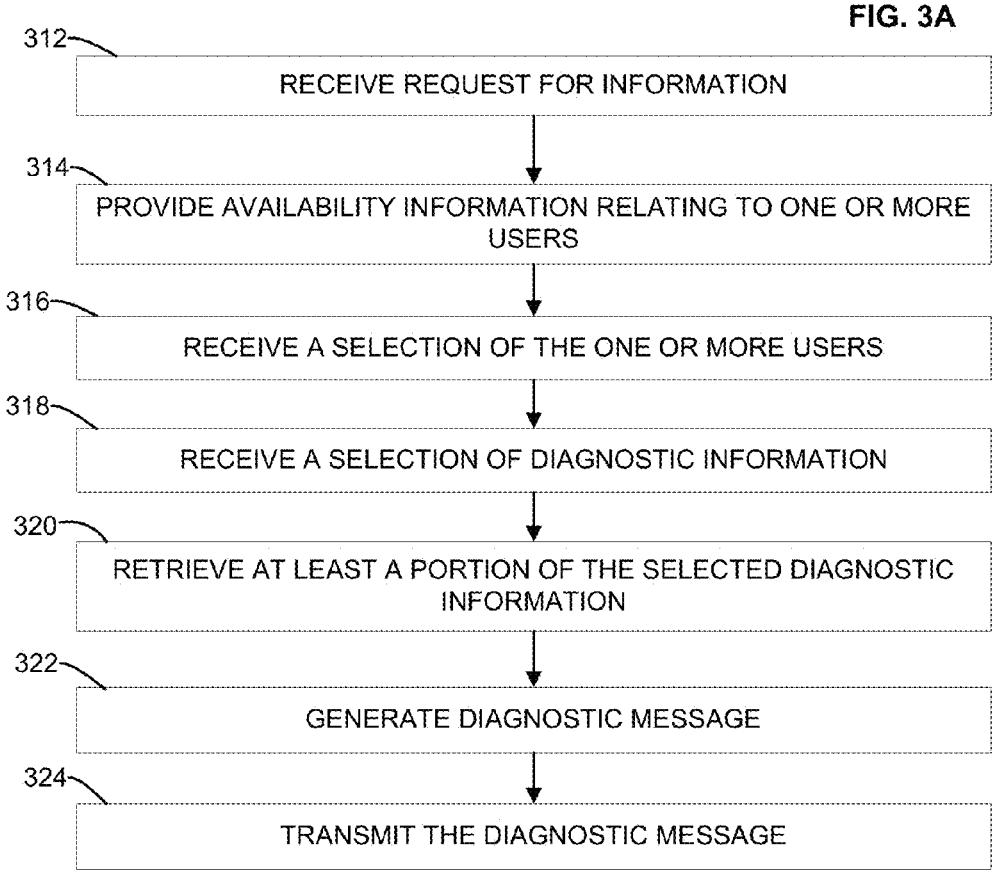
FIG. 3B is a flow chart of an exemplary method.

FIG. 3B illustrates an exemplary method for managing a diagnostic data based upon recipient availability. In an aspect, in step 312, a request for information, such as a message (e.g. diagnostic message, PHOTON, or the like), can be received, for example, by the computing device 104. As an example, the request can be received by the client device 102 or the user device 124. However, other devices and systems can be used to transmit the request. In an aspect, an interface is provided to allow a user/client to request a message. As an example, the client device 102 can include a user interface with a "request message" icon or engageable button. Other means of requesting the message can be used. As a further example, once a user/client selects the "request message" icon, the user/client can be prompted to provide and/or select particular diagnostic information to be included in the message.

In an aspect, in step 314, availability information relating to one or more of a plurality of users or intended recipients can be rendered to the client or requester. As an example, a calendar of availability for one or more on-call professionals, such as healthcare providers, can be rendered to the client or requester.

In an aspect, in step 316, a selection of at least one of the plurality of users or intended recipients can be received. In an aspect, the client selects/provides a desired recipient of the message based upon the availability information. As an example, the client can select an available recipient from a list of one or more on-call users. In an aspect, the selection/provision of availability information is received, for example, by the computing device 104.

In an aspect, the client selects/provides a particular information (e.g., diagnostic information, requester information, recipient information, etc.) to be included in the message and submits the request for the message. In an aspect, in step 318, the selection/provision of information is received, for example, by the computing device 104. As a further example, the computing device 104 can process the request to retrieve at least a portion of the selected information (e.g., diagnostic information), at step 320. In an aspect the diagnostic information can comprises one or more of patient data, medical data, and a medical image.

In an aspect, the computing device 104 can retrieve the selected/requested diagnostic information from any storage medium(s). As an example, at least a portion of the selected/requested diagnostic information is retrieved from the database 114. In an aspect, the user settings 118 associated with an intended recipient of the diagnostic message are applied to the selected/requested diagnostic information. For example, a particular user setting 118 may include pre-defined information fields that should be included in the messages that are sent to the user/recipient associated with the particular user setting 118. Accordingly, even though the selected/requested diagnostic information includes different information, the user setting 118 can take priority to retrieve a subset of the selected/requested diagnostic information to be included in the message.

In step 322, a diagnostic message can be generated. As an example, the diagnostic message can comprise the portion of the selected diagnostic information. However, any information can be included. In an aspect, the user settings 118 associated with an intended recipient of the diagnostic message are applied to the selected/requested diagnostic information. For example, a particular user setting 118 may include pre-defined information fields to be included in the messages that are sent to the user/recipient associated with the particular user setting 118. Accordingly, even though the selected/requested diagnostic information includes different information, the user setting 118 can take priority to retrieve a subset of the selected/requested diagnostic information to be included in the message.

In an aspect, computing device 104 and/or database 114 can comprise specialty templates for the messages. The specialty templates can be specifically created for each specialty in a particular profession, such as medicine/healthcare. For example, an orthopedic template can consist of basic patient information as well as x-rays. As a further example, a cardiology template can consist of basic patient information as well as an EKG or echocardiogram. As a further example, a gastroenterology template will consist of basic information as well as an abdominal x-ray or abdominal CT and perhaps lab information. The specialty templates can be created prior to implementation of the specific specialty message generation. Templates can be changed as needed. In an aspect, the requester of a message can select a pre-defined template for sending to an intended recipient.

In step 324, the message (e.g., diagnostic message) can be transmitted. As an example, the message can be transmitted to a recipient identified by the requester of the message. The message can be transmitted over any communication path or network such as the Internet and/or mobile telephone network.

In an aspect, the computing device 104 or other device can track a status of one or more transmitted messages. As an example, the following information can be tracked, time stamped, and or stored: date/time the message was generated/sent/received/forwarded/replied to; location (GPS) of requester/recipient; recipient device; receipt confirmation; read confirmation; no-read alert/feedback; and returned message alert. Other information and a feedback can be tracked/stored.

In an aspect, the scheduling application (e.g., Photon scheduling) can allow the client device 102 to set up appointments at a user's/consultant's office (e.g., office system 125). As an example, the client device 102 by accessing the scheduling data 130. As a further example, the user can reserve at least a portion of an available schedule for a particular set of patients (e.g., emergency room patients). In aspect, an emergency room provider, after requesting a diagnostic message, can use the scheduling application to send the diagnostic message directly to the office system 125 for direct uploading of diagnostic information into the user's office EMR software and provide the patient the appointment time, from the emergency room.

Figure 3C:
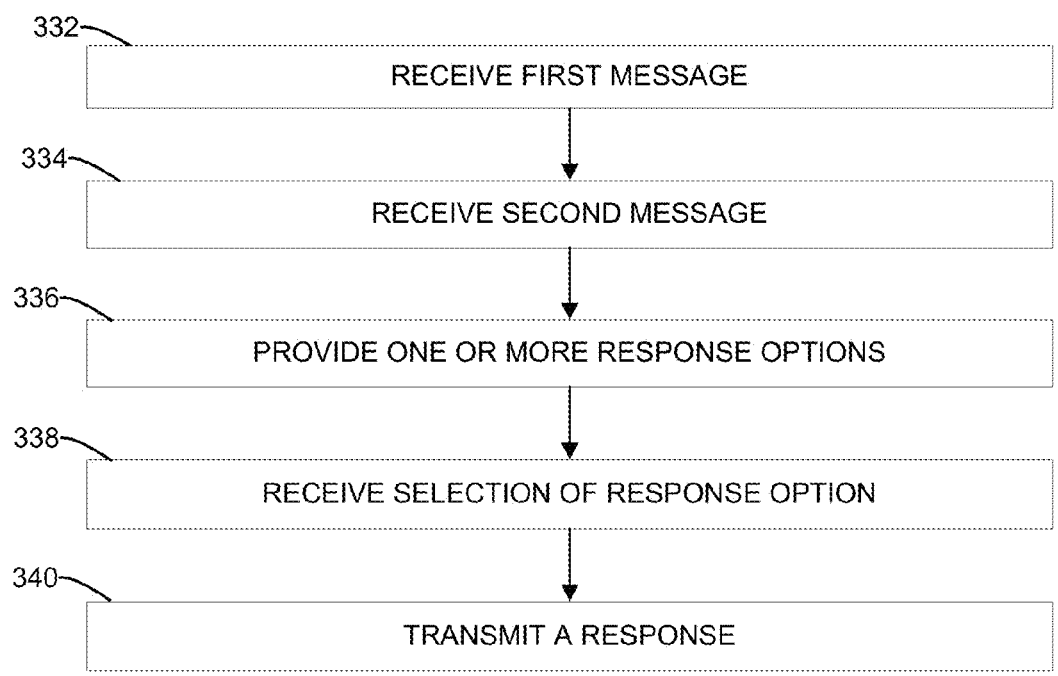
FIG. 3C is a flow chart of an exemplary method.

FIG. 3C illustrates an exemplary method for managing a diagnostic data based upon recipient availability. In step 332, a first message (e.g., diagnostic message) can be received by one or more users. As an example, the first message can comprise diagnostic information (e.g., injury description, images) to be reviewed by the recipient. As a further example, the first message can comprise a notification to retrieve diagnostic information from a remote location. In an aspect, the first message can be received by the client device 102. As an example, a confirmation message can be transmitted to a sender indicating whether the diagnostic message is received by a recipient device.

In another aspect, the user device 124 can be disposed in a location that is not equipped to communicate directly with the computing device 104. As an example, the client device 102 can operate as a proxy for the user device 104 when communicating with the computing device 104, the information system 108, and/or an office system 125. As a further example, the user device 124 may not be authenticated with one or more of the computing device 104, the information system 108, and/or an office system 125. As such, the user device 124 can communicate information to the client device 102 using a unique identifier (e.g., temporary or persistent) and the client device 102 can communication with one or more of the computing device 104, the information system 108, and/or an office system 125 on behalf of the user device 124. In an aspect, a user can locate contact information for a particular on-call physician. As an example, the user can transmit information to the on-call physician using standard communication networks (e.g., cellular, IP, media messaging, etc.). As a further example, the information transmitted can be tagged with an anonymous identifier that can later be associated with a particular medical record or patient file in a secure environment.

In yet another aspect, the first message of step 332 can be received by the client device 102 (e.g., a device associated on-call physician). Accordingly, a user of the client device can review the information comprised in the first message and can determine if the subject patient to whom the information relates should be transferred to a facility (e.g., emergency center, hospital, specialists office, etc.) for treatment and/or further analysis.

In step 334, a second message (e.g., diagnostic message, follow-up message) can be received by one or more users. As an example, the second message can comprise diagnostic information (e.g., injury description, images, supplemental information) to be reviewed by the recipient. As a further example, the second message can comprise a notification to retrieve diagnostic information from a remote location. In an aspect, the second message can be received by the client device 102. As an example, the second message can comprise supplemental information relating to the information comprised in the first message.

In step 336, one or more response options can be provided to the user. In an aspect, the response options can comprise one or more of a pre-defined diagnosis option, a forwarding the diagnostic message option, a communicating with sender option, and a generating a custom diagnosis option. Other options can be provided, such as an input option to allow the user to provide a particular response. As an example, at least one of the response options is customized based upon the diagnostic information.

In step 338, a selection of one of the plurality of response options can be received. In an aspect, the user can provide a particular information (e.g., consultation information, responses, feedback) to be included in a response message. As an example, the selection/provision of response information is received, for example, by the computing device 104. As a further example, the computing device 104 can process the response information to route the response to an appropriate recipient such as the client device 102.

In step 340, information, such as a response message (e.g., responsive diagnostic message), can be transmitted based upon the selection of the one of the plurality of response options. In an aspect, the message can be transmitted to the requester of the diagnostic information. As an example, the message can be transmitted or forwarded to a user for further review and consultation. As a further example, the message can be transmitted to the office system 125, wherein, for example, the information in the message can be used to update records stored in the office system 125.

In an aspect, in response to receiving the first message of step 332, the recipient can recommend that the subject patient be admitted in an emergency center. As an example, the subject patient can be admitted or checked-in to the emergency center. Detailed patient information can be collected and stored. Tests and procedures can be performed, such as X-rays and MRI's and the collected information can be electronically stored. In another aspect, a medical record or patient record can be created. As an example, the information comprised in the first message can be linked or associated with the newly created medical record, for example, by associated the anonymous identifier with the medical record. As a further example, information from one or more of the first message and the second message can be merged into a single record, such as a secure PDF. In an aspect, records can be stored on a secure HIPPA compliant server. As an example, a location such as a filename or URL can be used to identify and distinguish between records. Accordingly, the record can be subsequently accessed using the identifier.

Figure 4:
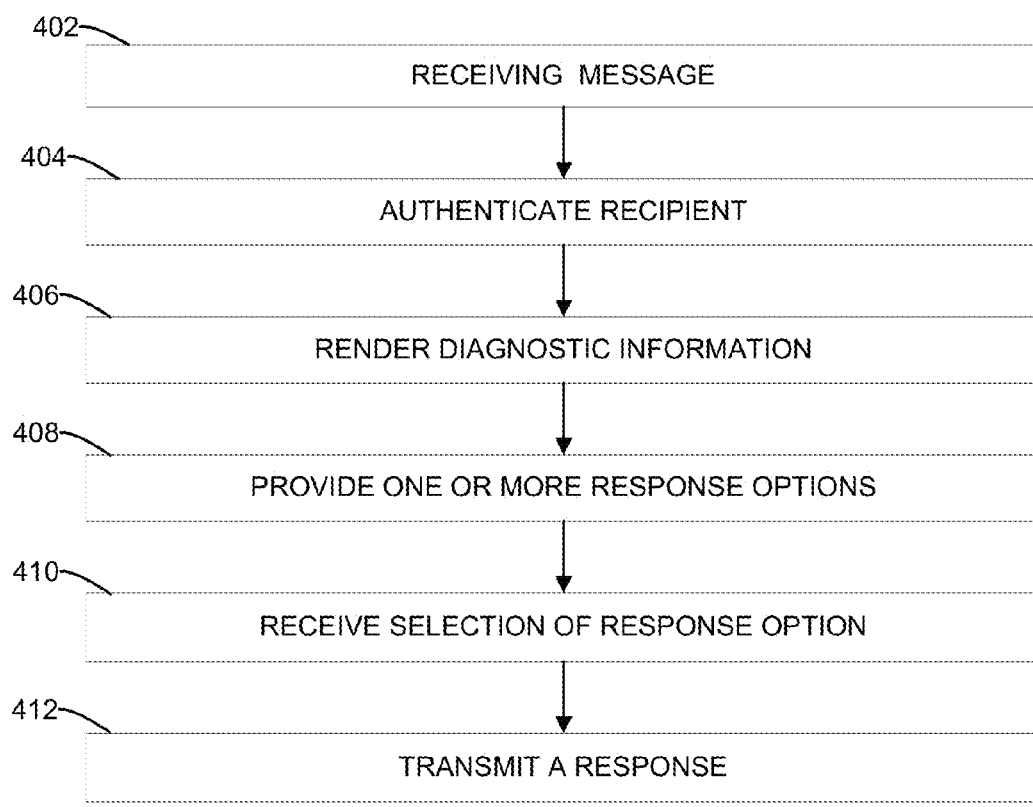
FIG. 4 is a flow chart of an exemplary method.

FIG. 4 illustrates an exemplary method for managing received diagnostic message. In an aspect, in step 402, a message (e.g., diagnostic message) can be received by one or more users. As an example, the message can comprise diagnostic information to be reviewed by the recipient. As a further example, the message can comprise a notification to retrieve diagnostic information from a remote location. In an aspect, the message can be received by the user device 124. As an example, a confirmation message can be transmitted to a sender indicating whether the diagnostic message is received by a recipient device.

In step 404, the diagnostic information can be rendered to the user. In an aspect, a recipient can be authenticated prior to rendering the diagnostic information. As an example, the diagnostic information can comprise audio, text, images, and video. As a further example, the recipient/user can interact with the user device 124 to review the diagnostic information. In an aspect, the diagnostic information can be classified and/or organized by pre-defined categories, such as objective, test results, images, historical information, or the like. As an example, a confirmation message can be transmitted to a sender indicating whether the diagnostic message has been reviewed by a user.

In step 406, one or more response options can be provided to the user. In an aspect, the response options can comprise one or more of a pre-defined diagnosis option, a forwarding the diagnostic message option, a communicating with sender option, and a generating a custom diagnosis option. Other options can be provided, such as an input option to allow the user to provide a particular response. As an example, at least one of the response options is customized based upon the diagnostic information.

In step 408, a selection of one of the plurality of response options can be received. In an aspect, the user can provide a particular information (e.g., consultation information, responses, feedback) to be included in a response message. As an example, the selection/provision of response information is received, for example, by the computing device 104. As a further example, the computing device 104 can process the response information to route the response to an appropriate recipient such as the client device 102.

In step 410, information such as a message can be transmitted based upon the selection of the one of the plurality of response options. In an aspect, the message can be transmitted to the requester of the diagnostic information. As an example, the message can be transmitted or forwarded to a user for further review and consultation. As a further example, the message can be transmitted to the office system 125, wherein, for example, the information in the message can be used to update records stored in the office system 125.

In an aspect, FIG. 5 illustrates a user interface 500 comprising a message notification 502. As an example, a user must be authenticated prior to viewing the message. As a further example, the user interface 500 can comprise a password input 504 for receiving a password to authenticate the user/recipient. In an aspect, the user interface 500 can comprise a keyboard or keypad to receive an input from the user (e.g., to ensure HIPPA compliance).

In an aspect, FIG. 6 illustrates a user interface 600 comprising a menu 602. As an example, the menus 602 can comprise options for navigating and organizing one or more diagnostic messages. In an aspect, a plurality of diagnostic messages can be organized by most recent 602a, all active messages 602b (e.g., message that require action), and/or all photons 602c. As an example, the interface 600 can comprise a homepage button 604, wherein a user can adjust settings.

In an aspect, FIG. 7 illustrates a user interface 700 comprising a plurality of active messages icons 702 representing messages that require action. As an example, the messages can comprise sender information, a date, and a time. Other information can be presented by the message icons.

In an aspect, FIG. 8 illustrates a user interface 800 comprising a plurality of setting options 802. As an example, the settings options can be presented as part of a "My Photon" page or homepage.

In an aspect, FIG. 9 illustrates a user interface 900 comprising an active message notification 902. As an example, the notification 902 can comprise options, such as view now 904 and/or a scrolling option (e.g., next 906) to facilitate the navigation through a plurality of notifications. As a further example, the user interface 900 can also comprise universal options 908 to facilitate navigation between various user interface screens.

In an aspect, FIG. 10 illustrates a user interface 1000 comprising a message header 1002 identifying the particular message. The user interface 1000 can comprise diagnostic information, wherein the diagnostic information can be organized or categorized. As an example, the categories can comprise history 1004, objective 1006, test/EKG/X-rays 1008 and/or other classifications. As a further example, a plurality of response options 1010 can be provided to the user. In an aspect, the response options 1010 can comprise call 1012, transfer 1014, and/or reply 1016. Other options can be provided.

Figure 11:
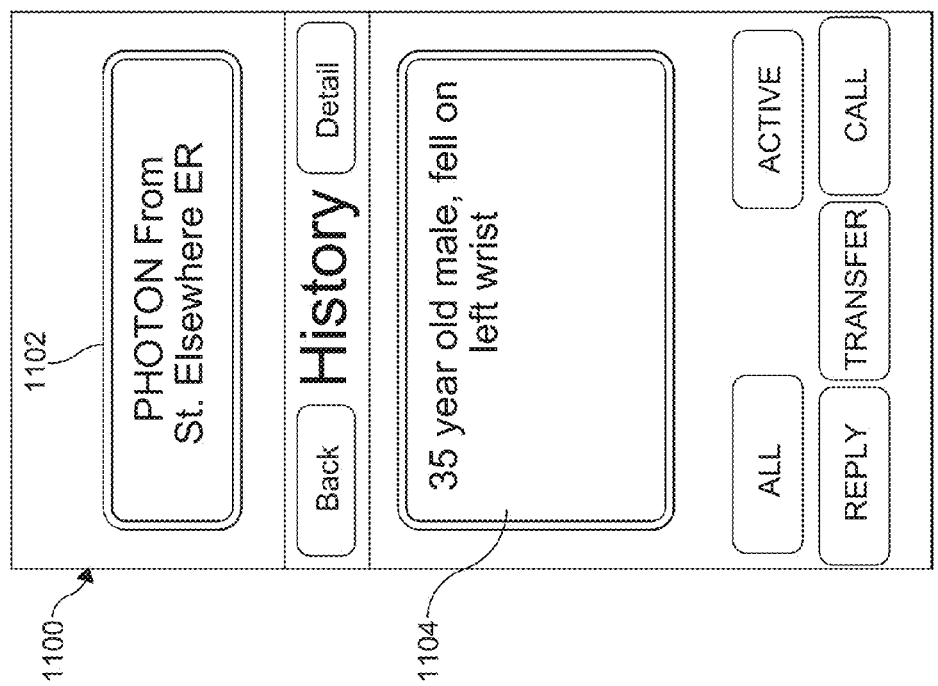
FIG. 11 is a representation of a user interface.

In an aspect, FIG. 11 illustrates a user interface 1100 comprising a message header 1102 identifying the particular message. In an aspect, the user interface 1100 can comprise historical information 1104, such as a medical history, a background to a particular incident, and/or past diagnostic information. Other information can be provided.

Figure 12:
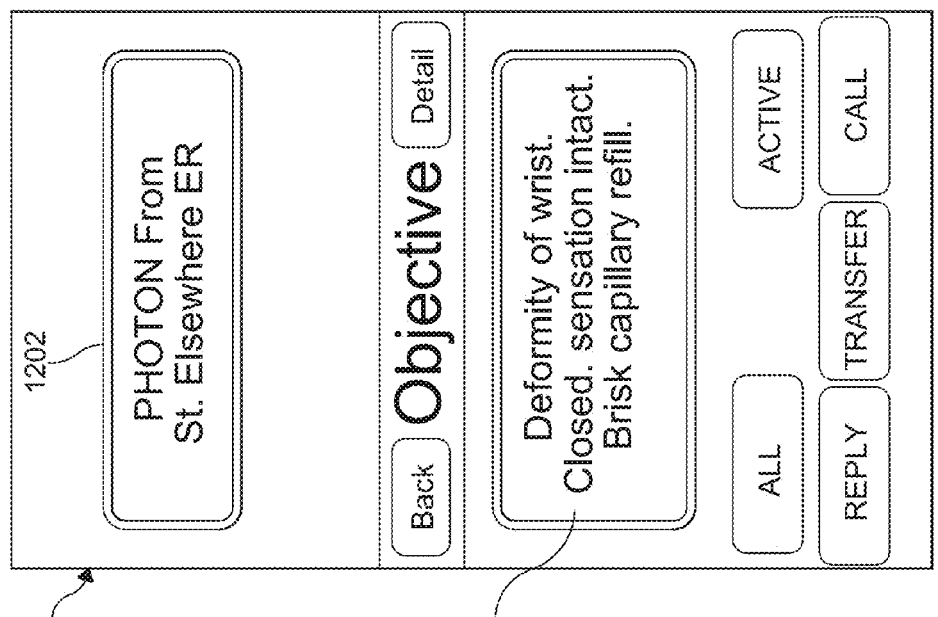
FIG. 12 is a representation of a user interface.

In an aspect FIG. 12 illustrates a user interface 1200 comprising a message header 1202 identifying a particular message. In an aspect, the user interface 1200 can comprise objective information 1204, such as diagnostic information, medical information, and/or a background to a particular incident. Other information can be provided.

In an aspect, FIG. 13 illustrates a user interface 1300 comprising a message header 1302 identifying a particular message. In an aspect, the user interface 1300 can comprise diagnostic information 1304, such as lab results 1306, EKG 1308, and/or X-ray 1310. Other information can be provided.

In an aspect, FIG. 14 illustrates a user interface 1400 comprising a message header 1402 identifying a particular message. In an aspect, the user interface 1400 can comprise detailed lab information 1404, such as lab results or other test information. Other information can be provided.

Figure 16:
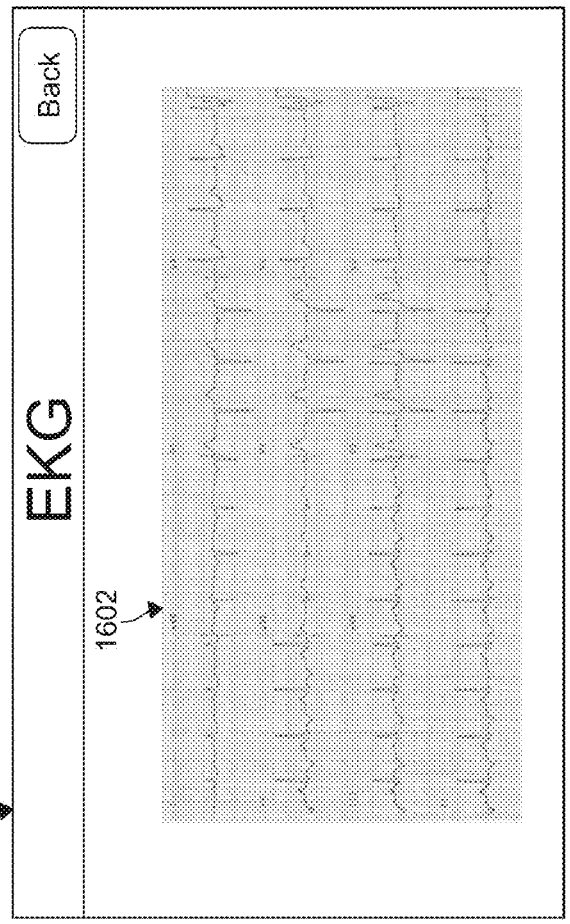
FIG. 16 is a representation of a user interface.
Figure 15:
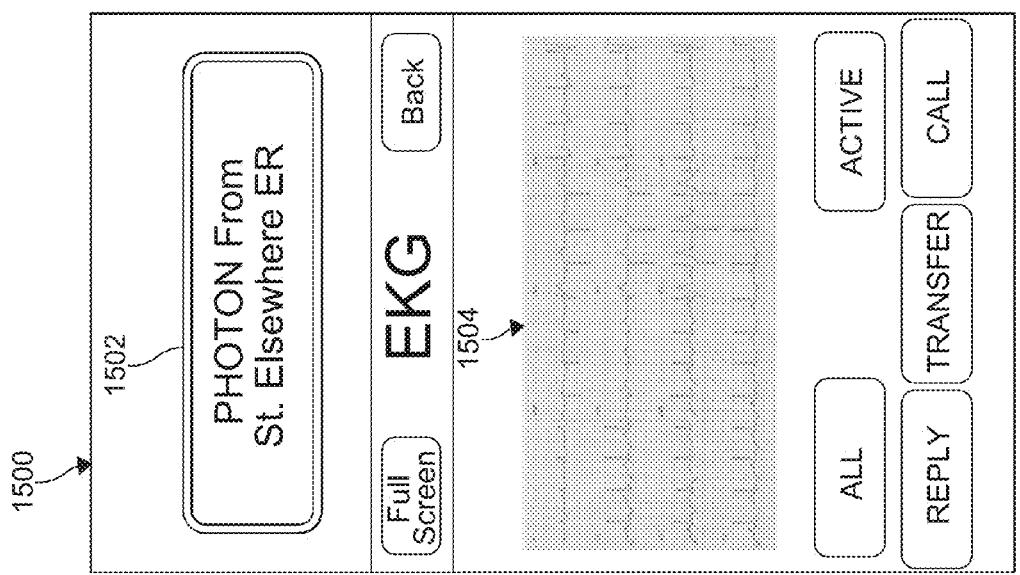
FIG. 15 is a representation of a user interface.

In an aspect, FIG. 15 illustrates a user interface 1500 comprising a message header 1502 identifying a particular message. In an aspect, the user interface 1500 can comprise detailed monitoring information 1504, such as EKG or other test information. Other information can be provided. In an aspect, FIG. 16 illustrates a user interface 1600 can render an enlarged image 1602 representing a test result or medical information.

Figures 17, 18:
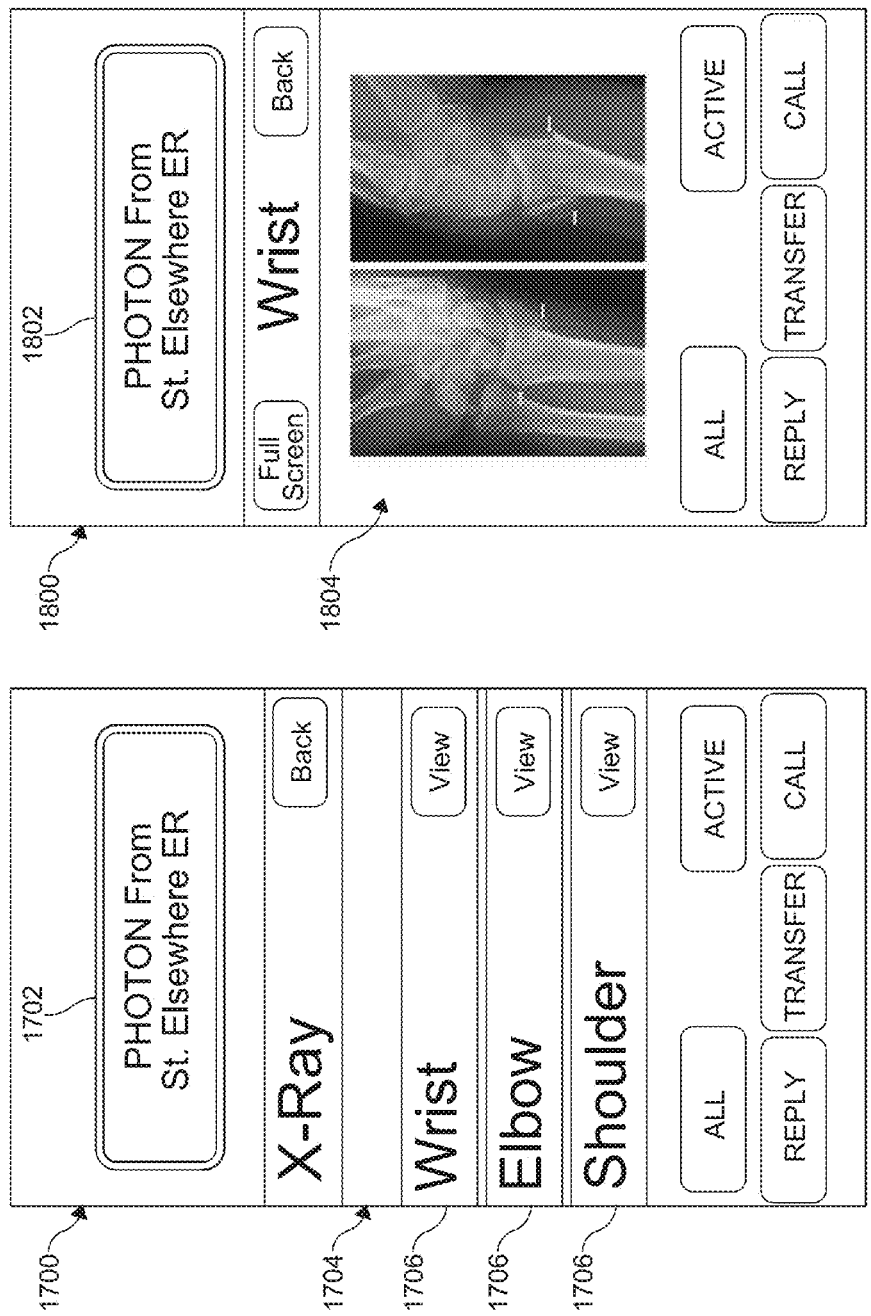
FIG. 17 is a representation of a user interface.
FIG. 18 is a representation of a user interface.

In an aspect, FIG. 17 illustrates a user interface 1700 comprising a message header 1702 identifying a particular message. In an aspect, the user interface 1700 can comprise detailed imaging information 1704, such as X-rays or other test information. Other information can be provided. In an aspect, a plurality of images 1706 can be classified and rendered for a user to view.

In an aspect, FIG. 18 illustrates a user interface 1800 comprising a message header 1802 identifying a particular message. In an aspect, the user interface 1800 can comprise a rendered image 1804, such as an X-ray or other test information. Other information can be provided.

In an aspect, FIG. 19 illustrates a user interface 1900. In an aspect, a user can select to transfer or forward the diagnostic message and/or diagnostic information to another user or recipient. As an example, the user interface 1900 can provide forwarding options and/or selectable destinations such as an EMR 1902*a*, a physician 1902*b*, an office 1902*c* (e.g., the office system 125), or other destination. As a further example, the user interface 1900 can comprise a confirmation button 1904 for initiating the transfer once a intended recipient has been provided.

In an aspect, FIG. 20 illustrates a user interface 2000 comprising a contact list, including a contact classification header 2002 and an organized list 2004 of potential recipients of a forwarded message and/or information.

Figure 22:
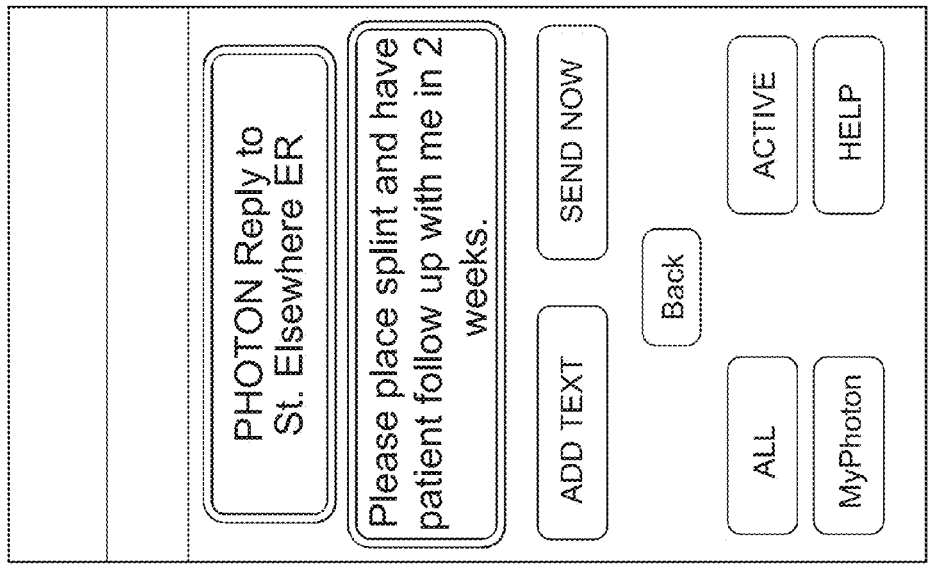
FIG. 22 is a representation of a user interface.
Figure 21:
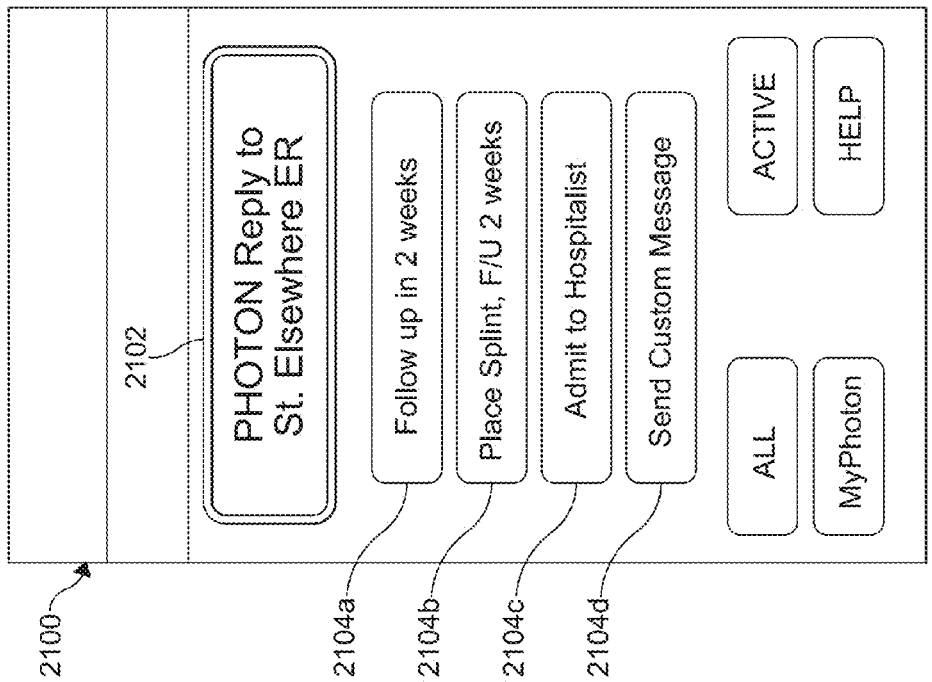
FIG. 21 is a representation of a user interface.
Figure 24:
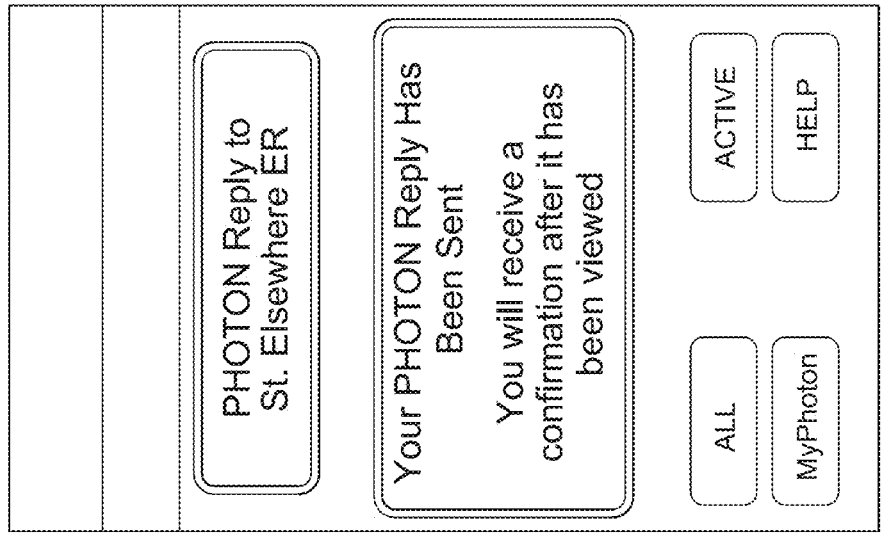
FIG. 24 is a representation of a user interface.
Figure 23:
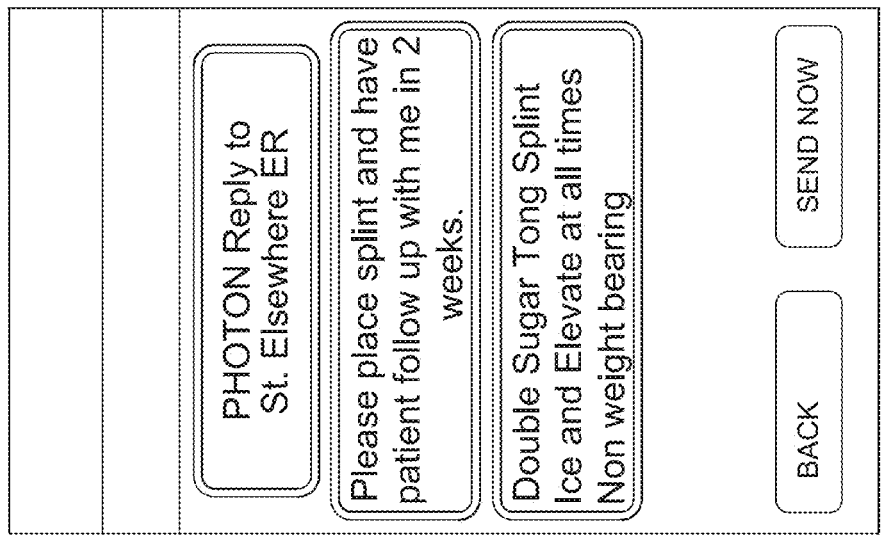
FIG. 23 is a representation of a user interface.

In an aspect, FIG. 21 illustrates a user interface 2100 comprising a message header 2102 identifying a particular message. In an aspect, a user can select to provide a reply to the diagnostic message. As an example, the user interface 2100 can comprise pre-defined response options 2104*a*, 2104*b*, 2104*c*, 2104*d*. In an aspect, the response options 2104*a*, 2104*b*, 2104*c*, 2104*d* can be defined based upon the diagnostic information included in the message. As an example, the response options 2104*a*, 2104*b*, 2104*c*, 2104*d* can comprise a customizable response option 2104*d* to allow a user to create a customized response message, as shown in further detail in FIGS. 22-23. In an aspect, once a response message has been generated (FIG. 23), the response message can be transmitted to a recipient. As an example, a confirmation can be provided to the user, as shown in FIG. 24, thereby completing an exemplary cycle of consultation.

FIG. 25 illustrates a messaging screen (e.g., a Photon lite screen). In an aspect, the messaging screen can facilitate secure and unsecure communication of information to one or more devices such as client devices 102 and/or user devices 124, for example. In another aspect, the messaging screen can be rendered via user device 124 that is disposed in a location that is not equipped to communicate directly with the computing device 104. As an example, the client device 102 can operate as a proxy for the user device 104 when communicating with the computing device 104, the information system 108, and/or an office system 125. As a further example, the user device 124 may not be authenticated with one or more of the computing device 104, the information system 108, and/ or an office system 125. As such, the user device 124 can communicate information to the client device 102 using a unique identifier (e.g., temporary or persistent) and the client device 102 can communication with one or more of the computing device 104, the information system 108, and/or an office system 125 on behalf of the user device 124. In an aspect, a user can locate contact information for a particular on-call physician. As an example, the user can transmit information to the on-call physician using standard communication networks (e.g. cellular, IP, media messaging, etc.). As a further example, the information transmitted can be tagged with an identifier (e.g., anonymous) that can later be associated with a particular medical record or patient file in a secure environment.

In an aspect, a patient code 2502 can be provided (e.g., manually or automatically) as an identifier for tracking information associated with the patient code 2502. As an example, a patient name 2504 can be provided (e.g., inputted), as opposed to pulling patient information from the hospital EMR. As a further example, information such as a description of the patient or medical issue/condition can be provided. In another aspect, an urgency option 2602 can be provided, as shown in FIG. 26. As an example, the urgency option 2602 can be rendered to a user of the messaging screen, whereby a selection of the urgency option indicates a need for immediate care of the subject of the message. As a further example, description information and/or the urgency option 2602 can be associated with the patient code 2502 for associating the images with a particular patient. In a further aspect, one or more images can be provided (e.g., loaded, attached to the message, etc.), as shown in FIG. 27. As an example, a camera can be used to capture an image. The image can comprise video, audio, still images, or the like. Captured images can be encrypted and not saved to the device in a readable manner (or stored in a secure hidden directory). Once the capture images are transmitted, the images can be removed from the capturing device. As a further example, one or more captured images can be associated with the patient code 2502 for associating the images with a particular patient.

In an aspect, the systems and methods described herein provide a simple "click-by-click" process for both the emergency room provider and the consultant. With regards to the emergency room physician, once the scheduling packages open, a first click can comprise opening an orthopedic call schedule. A second click can comprise sending a Photon to the orthopedist that is on call, thereby resulting in a two-click process. With regards to the consultant physician, once the consultant has received notification that the Photon is now on a smart device, the consultant can log into an interface application (e.g., the Photon application), constituting a first click. If there is only one Photon available, it will automatically be populated. The consultant can be able to review all the relevant information instantly. The consultant can then click on an action button or transmit button to send the appropriate response, thereby constituting a second click. However, automation of certain events, such as push notifications, populating an interface, displaying options, and the like can facilitate a single click operation.

In an aspect, the systems and methods disclosed herein can be integrated with one or more scheduling products to facilitate a compliant scheduling program comprising the ability to send compliant images and messages bidirectionally, and save such messages into an EMR. As an example, users can use Photons to transmit a "facesheet" for billing, wherein the can comprise a patient's demographics, insurance information, contact information.

Photons can be sent to virtually anyone, from a health care provider, to industry (we can parse out non-HIPAA compliant information). As an example, in-theatre military healthcare applications can leverage the benefits of the systems and methods disclosed herein.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications are referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method for Health Insurance Portability and Accountability (HIPPA)-compliant messaging, the method comprising:
   authenticating a user at a server, based on at least first credentials received from a first device;
   receiving a request for a consultation at the server, the request received from the first device;
   causing availability information for a plurality of healthcare providers to be rendered on the first device;
   receiving an indication, from the first device, that the user selected a first healthcare provider of the plurality of healthcare providers based on at least the availability information;
   securely receiving a selection of diagnostic information from the first device, the diagnostic information comprising at least one of patient data, medical data, or a medical image;
   determining a user setting associated with the first healthcare provider, the user setting identifying a specialty of the first healthcare provider and an information field to be included in a message to the first healthcare provider, wherein the information field is configured to be populated by the server with a portion of the diagnostic information;
   identifying a subset of the diagnostic information based on at least the user setting;
   retrieving the diagnostic information subset;
   causing the first healthcare provider to be notified of the request for consultation;
   authenticating the first healthcare provider at the server, based on at least second credentials received from a second device;
   generating the message, wherein the message comprises the diagnostic information subset and the populated information field;
   causing the message to be rendered on the second mobile device;
   causing a pre-defined diagnosis option to be rendered on the second device, the pre-defined diagnosis option based on at least a portion of the diagnostic information subset, wherein the first healthcare provider can provide consultation by selected the pre-defined diagnosis option;
   determining that the pre-defined diagnosis option was selected at the second device;
   transmitting, to the first device, a second message notification; and
   causing a diagnosis to be rendered on the first device, wherein the diagnosis is based on the selected pre-defined diagnosis option.

2. The method of claim 1, wherein the message comprises an encrypted image captured by a camera associated with the first device, wherein the first device does not retain a copy of the encrypted image after transmitting the encrypted image to the server.

3. The method of claim 1, further comprising:
   causing a response option to be rendered on the second device, the response option comprising at least one of a reply option, a call option to call the user, or a forwarding option; and
   notifying the first device of a response selection by the second device, the response selection based on at least the response option.

4. The method of claim 1, wherein the diagnostic information comprises a first diagnostic information and the user setting indicates that the healthcare provider does not want to receive the first diagnostic information, such that the diagnostic information subset does not include the first diagnostic information.

5. The method of claim 1, further comprising:
   in response to receiving the indication, causing scheduling data associated with the consultant be rendered on the first device;
   receiving an appointment time selection from the first device, the appointment time selection based on at least the scheduling data; and
   causing the message and the appointment time to be incorporated into an emergency medical record system, wherein the appointment time is for a patient associated with the request for consultation.

6. The method of claim 1, further comprising causing a response to be rendered on the first device, the response including at least one of a recommendation to perform a test, implement a procedure, admit a patient associated with the request, or receive more information regarding the patient.

7. The method of claim 1, wherein the request for consultation is received by the first device from a user device that is not authenticated with the server, and
   the first device operates as a proxy when communicating the request for consultation to the server, the first device using a unique identifier associated with the user device to communicate with the user device.

8. The method of claim 1, further comprising causing an urgency option to be rendered on the second device, the urgency option indicating a need for immediate care of a patient associated with the request for consultation.

9. The method of claim 1, further comprising a billing facesheet to be transmitted to the second device, the billing facesheet comprising contact information and insurance information for a patient associated with the request.

10. A method for Health Insurance Portability and Accountability (HIPPA)-compliant messaging, the method comprising:
   authenticating a user at a server, based on at least first credentials received from a requesting device;
   receiving a request for consultation with a first healthcare provider, at the server, from the requesting device;
   securely receiving a selection of diagnostic information from the requesting device, the diagnostic information comprising at least one of patient data, medical data, or a medical image;
   determining a user setting associated with the first healthcare provider, the user setting identifying a specialty of the first healthcare provider and an information field populated with a portion of the diagnostic information to be included in a message to the first consultant;
   identifying a subset of the diagnostic information based on at least the user setting;
   causing the first healthcare provider to be notified of the request for consultation;
   causing a forwarding option to be rendered on the first mobile device;
   receiving a forwarding instruction to forward the message to a second healthcare provider, from the first mobile device;
   causing the second healthcare provider to be notified of the request for consultation;
   authenticating the second healthcare provider at the server based on at least a second credential received from a second mobile device;
   generating the message, wherein the message is indicative of the selected diagnostic information subset;
   causing the message to be rendered on the second mobile device;
   causing a response option to be rendered on the second mobile device, the response option including at least a pre-defined diagnosis option based on at least a portion of the selected diagnostic information subset, wherein the second healthcare provider can provide consultation by selecting the pre-defined diagnosis option;
   receiving a response from the second mobile device based on at least the response option; and
   causing an indication of the response to be rendered on the first mobile device.

11. The method of claim 10, wherein the request comprises an encrypted image captured by a camera associated with the requesting device, wherein the requesting device does not retain a copy of the encrypted image after transmitting the encrypted image to the server.

12. The method of claim 10, further comprising:
   causing scheduling data associated with the second consultant to be rendered on the requesting device;
   receiving an appointment time selection from the requesting device, the appointment time selection based on at least the scheduling data; and
   causing the message and the appointment time to be incorporated into an emergency medical record system, wherein the appointment time is for a patient associated with the request for consultation.

13. The method of claim 10, further comprising causing availability information for a plurality of healthcare providers to be rendered on the first mobile device, the plurality of healthcare providers including the second healthcare provider, wherein the forwarding instruction is based upon the availability information.

14. The method of claim 10, wherein the diagnostic information comprises a first diagnostic information and the user setting indicates that the healthcare provider does not want to receive the first diagnostic information, such that the diagnostic information subset does not include the first diagnostic information.

15. The method of claim 10, further comprising:
   authenticating the first healthcare provider at the server based on at least a third credential received from the first mobile device; and
   causing the message to be rendered on the first mobile device,
   wherein the forwarding instruction is received subsequent to the rendering of the message on the first mobile device.

16. The method of claim 10, wherein the response includes at least one of a recommendation to perform a test, implement a procedure, or admit a patient associated with the request for consultation.

17. The method of claim 10, wherein receiving the response comprises determining that the second healthcare provider selected the pre-defined diagnosis option, wherein the response comprises a diagnosis based on at least a selection of a pre-defined diagnosis option at the third mobile device.

18. The method of claim 10, further comprising causing an urgency option to be rendered on at least one of the first mobile device or the second mobile device, the urgency option indicating a need for immediate care of a subject of the request.

19. The method of claim 10, further comprising a billing facesheet to be transmitted to the second mobile device, the billing facesheet comprising contact information and insurance information for a patient associated with the request for consultation.

20. The method of claim 10, wherein the response option further comprises at least one of a reply option, a call option to call the user, or a forwarding option.

21. The method of claim 10, wherein the request for consultation is received by the requesting device from a user device that is not authenticated with the server, and
   the requesting device operates as a proxy when communicating the request for consultation to the server, wherein the requesting device uses a unique identifier associated with the user device to communicate with the user device.

22. A method for secure messaging between a user and a healthcare provider, the method comprising:
   authenticating the user based on first credentials received from a requesting device;
   receiving a request for a consultation from the requesting device;
   causing availability information for a plurality of healthcare providers to be rendered on the requesting device;
   receiving a first indication from the requesting device that the user selected a first healthcare provider of the plurality of healthcare providers based on at least the availability information;

receiving a selection of diagnostic information from the requesting device, the diagnostic information comprising at least one of patient data, medical data, or a medical image;

determining a user setting associated with the first healthcare provider, the user setting identifying a specialty of the first healthcare provider and an information field to be populated with a portion of the diagnostic information;

identifying a subset of the diagnostic information based on the user setting;

causing a notification of the request for consultation to be rendered on a mobile device;

authenticating the first healthcare provider at the server based on second credentials received from the mobile device;

generating the message based on at least the diagnostic information subset;

causing the message to be rendered on the mobile device;

causing a response option to be rendered on the mobile device, the response option including a pre-defined diagnosis option based upon at least a portion of the diagnostic information subset, wherein the first healthcare provider can provide consultation by selecting the pre-defined diagnosis option;

receiving a response from the mobile device based on at least a selection of the response option at the mobile device; and causing a response notification to be rendered on the requesting device, the response notification based on at least the response.

23. The method of claim 22, wherein the message comprises an encrypted image captured by a camera associated with the requesting device, wherein the requesting device does not retain a copy of the encrypted image after transmitting the encrypted image to the server.

24. The method of claim 22, further comprising:
in response to receiving the first indication, causing scheduling data associated with the first healthcare provider be rendered on the requesting device;
receiving an appointment time selection from the requesting device, the appointment time selection based on at least the scheduling data; and
causing the message and the appointment time to be incorporated into an emergency medical record system, wherein the appointment time is for a patient associated with the request for consultation.

25. The method of claim 22, further comprising retrieving the diagnostic information subset at the server.

26. The method of claim 22, wherein the diagnostic information comprises a first diagnostic information and the user setting indicates that the healthcare provider does not want to receive the first diagnostic information, such that the diagnostic information subset does not include the first diagnostic information.

27. The method of claim 22, wherein the request for consultation is received by the requesting device from a user device that is not authenticated with the server, and the requesting device operates as a proxy when communicating the request for consultation to the server, wherein the requesting device uses a unique identifier associated with the user device to communicate with the user device.

28. A method for Health Insurance Portability and Accountability (HIPPA)-compliant messaging, the comprising:
authenticating a user based on at least first credentials received from a requesting device;
receiving a request for consultation from the first mobile device;
causing availability information for a plurality of healthcare providers to be rendered on the first mobile device;
receiving an indication, from the requesting device, that the user selected a first healthcare provider of the plurality of healthcare providers based at least on the availability information;
securely receiving a selection of diagnostic information from the requesting device, the diagnostic information comprising at least one of patient data, medical data, or a medical image;
determining a user setting associated with the first healthcare provider, the user setting identifying an information field to be included in a message, wherein the information field is configured to be populated by the processor with a portion of the diagnostic information;
identifying a subset of the diagnostic information based on at least the user setting, wherein, based on the information field, the diagnostic information subset comprises a first diagnostic information that was not identified by the diagnostic information selection and the diagnostic information selection does not include a second diagnostic information, the second diagnostic information identified by the diagnostic information selection;
retrieving the diagnostic information subset;
causing the first healthcare professional to be notified of the request for consultation;
authenticating the first healthcare professional based on at least second credentials received from a mobile device;
generating the message, wherein the message comprises the diagnostic information subset;
causing the message to be rendered on the mobile device;
causing a pre-defined diagnosis option to be rendered on the mobile device, the pre-defined diagnosis option based on at least a portion of the diagnostic information subset, wherein the healthcare provider can provide consultation by selecting the pre-defined diagnosis option;
determining that the pre-defined diagnosis option was selected at the mobile device;
transmitting, to the requesting device, a second message notification; and
causing a diagnosis to be rendered on the requesting device, wherein the diagnosis is based on the selected pre-defined diagnosis option.

* * * * *